US008975442B2

(12) United States Patent
Leproust et al.

(10) Patent No.: US 8,975,442 B2
(45) Date of Patent: Mar. 10, 2015

(54) PROCESS FOR THE PREPARATION OF AND CRYSTALLINE FORMS OF OPTICAL ENANTIOMERS OF MODAFINIL

(71) Applicant: Teva Sante, La Defense Cedex (FR)

(72) Inventors: Pierre Leproust, Creteil (FR); Olivier Neckebrock, Pontault Combault (FR)

(73) Assignee: Teva Sante, La Defense Cedex (Paris) (FR)

( * ) Notice: Subject to any disclaimer, the term of this patent is extended or adjusted under 35 U.S.C. 154(b) by 0 days.

(21) Appl. No.: 14/012,363

(22) Filed: Aug. 28, 2013

(65) Prior Publication Data

US 2014/0031589 A1 Jan. 30, 2014

Related U.S. Application Data

(60) Continuation of application No. 13/858,483, filed on Apr. 8, 2013, now Pat. No. 8,729,305, which is a continuation of application No. 12/507,631, filed on Jul. 22, 2009, now abandoned, which is a division of application No. 11/474,859, filed on Jun. 26, 2006, now abandoned, which is a continuation of application No. 10/539,918, filed as application No. PCT/FR03/03799 on Dec. 18, 2003, now Pat. No. 7,132,570.

(30) Foreign Application Priority Data

Dec. 20, 2002 (FR) ...................................... 02 16412

(51) Int. Cl.
*C07C 315/06* (2006.01)
*C07C 317/28* (2006.01)
*C07C 315/04* (2006.01)

(52) U.S. Cl.
CPC ............. *C07C 317/28* (2013.01); *C07C 315/04* (2013.01); *C07C 315/06* (2013.01); *C07B 2200/07* (2013.01); *C07B 2200/13* (2013.01)
USPC ....................................................... 564/162

(58) Field of Classification Search
CPC ............................ C07C 315/06; C07C 317/28
USPC ....................................................... 564/162
See application file for complete search history.

(56) References Cited

U.S. PATENT DOCUMENTS

| | | | |
|---|---|---|---|
| 1,905,990 A | 4/1933 | Aeschlimann | |
| 4,177,290 A | 12/1979 | Lafon | |
| 4,755,522 A | 7/1988 | Lafon | |
| 4,927,855 A | 5/1990 | Lafon | |
| 4,983,599 A | 1/1991 | Lafon | |
| 5,250,543 A | 10/1993 | Lafon | |
| 6,489,363 B2 | 12/2002 | Jacobs et al. | |
| 6,605,636 B2 | 8/2003 | Aronhime et al. | |
| 6,849,120 B2 | 2/2005 | Singer et al. | |
| 6,894,171 B1 | 5/2005 | Bauer et al. | |
| 6,919,367 B2 | 7/2005 | Bacon et al. | |
| 6,919,378 B2 | 7/2005 | Jacobs et al. | |
| 6,992,219 B2 | 1/2006 | Broquaire et al. | |
| 7,132,570 B2 | 11/2006 | Neckebrock et al. | |
| 7,235,691 B2 * | 6/2007 | Ceausu et al. | ................ 564/162 |
| 7,244,748 B2 | 7/2007 | Borgens et al. | |
| 7,608,222 B2 | 10/2009 | Blomsma et al. | |
| 7,649,020 B2 | 1/2010 | Broquaire et al. | |
| 7,702,071 B2 | 4/2010 | Blomsma et al. | |
| 2001/0036640 A1 | 11/2001 | D'Amico | |
| 2002/0043207 A1 * | 4/2002 | Singer et al. | .................... 117/68 |
| 2002/0048610 A1 | 4/2002 | Cima et al. | |
| 2003/0022940 A1 | 1/2003 | Corvari et al. | |
| 2003/0124028 A1 | 7/2003 | Carlson et al. | |
| 2003/0220403 A1 | 11/2003 | Corvari et al. | |
| 2004/0048931 A1 | 3/2004 | Heacock et al. | |
| 2004/0102523 A1 | 5/2004 | Broquaire et al. | |
| 2007/0021510 A1 | 1/2007 | Hickey et al. | |
| 2007/0293702 A1 | 12/2007 | Braude et al. | |
| 2008/0269264 A1 | 10/2008 | Selbo | |
| 2009/0018202 A1 | 1/2009 | Hickey et al. | |
| 2009/0105346 A1 | 4/2009 | Jegorov | |
| 2009/0123545 A1 | 5/2009 | Ron et al. | |
| 2009/0156855 A1 | 6/2009 | Barreca et al. | |
| 2009/0281192 A1 | 11/2009 | Neckebrock et al. | |
| 2009/0281193 A1 | 11/2009 | Neckebrock et al. | |
| 2010/0022653 A1 | 1/2010 | Neckebrock et al. | |
| 2010/0048718 A1 | 2/2010 | Neckebrock et al. | |
| 2010/0048719 A1 | 2/2010 | Neckebrock et al. | |
| 2010/0048720 A1 | 2/2010 | Neckebrock et al. | |
| 2010/0234468 A1 | 9/2010 | Gaitonde et al. | |

FOREIGN PATENT DOCUMENTS

| | | |
|---|---|---|
| EP | 0 720 595 B1 | 12/1998 |
| FR | 2 593 809 | 8/1987 |
| FR | 0 216 412 | 12/2002 |

(Continued)

OTHER PUBLICATIONS

Amiard, G., "No. 81.—Sur le dédoublement direct de la thréonine, par entrainement," *Bull. Soc. Chim. Fr.*, 1956, 447 (no English abstract).
Armodafinil Search, "Preliminary results from registry number search," Apr. 10, 2006, 1-36 and 1-296.
Bernstein, J., "Polymorphism in molecular crystals," *University Press*, UK, 2002, Chapter 10, 297-307.
Coquerel, G., "Review on the heterogeneous equilibria between condensed phases in binary systems of enantiomers," *Enantiomers, Gordon & Breach Science Publishers*, 2000, 5, 481-498.
Collet, A., et al., "Optical resolution by direct crystallization of enantiomer mixtures," *Chem. Rev.*, 1980, 80(3), 215-230.
Courvoisier, L., et al., "Influence of the process on the mechanisms and the performances of the preferential crystallization: example with (±)-5-4(4-Bromophenyl)-5-methylhydantoin," *Chemistry Letters*, 2001, 364-365.

(Continued)

*Primary Examiner* — Shailendra Kumar

(57) ABSTRACT

The invention relates to a polymorphic form of (−)-modafinil that produces a powder X-ray diffraction spectrum comprising intensity peaks corresponding to interplanar spacings of about 14.14, 10.66, 7.80 and 4.02 Å, and a process for the preparation thereof.

15 Claims, 16 Drawing Sheets

(56) References Cited

FOREIGN PATENT DOCUMENTS

| | | |
|---|---|---|
| FR | 2 849 029 | 6/2004 |
| GB | 1 197 809 | 7/1970 |
| WO | WO01/22961 A1 | 4/2001 |
| WO | WO02/10125 A1 | 2/2002 |
| WO | WO2004/060858 A1 | 7/2004 |
| WO | WO2005/023198 A2 | 3/2005 |
| WO | WO2005/077894 A1 | 8/2005 |
| WO | WO2007/098273 A2 | 8/2007 |
| WO | WO2007/103221 A2 | 9/2007 |
| WO | WO2008/149141 A2 | 12/2008 |
| WO | WO2009/024863 A2 | 2/2009 |
| WO | WO2009/025791 A2 | 2/2009 |
| WO | WO2009/045488 A2 | 4/2009 |
| WO | WO2009/090663 A1 | 7/2009 |

OTHER PUBLICATIONS

De Min., M., et al., "Chiral resolutions, asymmetric synthesis and amplification of enantiomeric excess," *J. Chem. Phys.*, 1988, 85, 603-619.

Donovan, J.L., et al., "Chiral analysis of d- and l-modafinil in human serum: application to human pharmacokinetic studies," *Ther. Drug Monitoring*, 2003, 25, 197-202.

In, Y., et al., "Crystal and molecular structure of an (S)-(+)-enantiomer of modafinil, a novel wake-promoting agent," *Chem. Pharm. Bull.*, 2004, 52(10), 1186-1189.

Kim, S., et al., "A simple and mild esterification method for carboxylic acids using mixed carboxylic-carbonic anhydrides," *Am. Chem. Soc.*, 1985, 560-565.

Ndzié, E., et al., "An efficient access to the enantiomers of α-methyl-4-carboxyphenylglycine via a hydantoin route using a practical variant of preferential crystallization AS3PC (auto seeded programmed polythermic preferential crystallization)," *Tetrahedron Asymmetry*, 1997, 8(17), 2913-2920.

Prisinzano, T., et al., "Synthesis and determination of the absolute configuration of the enantiomers of modafinil," *Tetrahedron: Asymmetry*, 2004, 15, 1053-058.

Raynal, H., et al., "Disposition of modafinil enantiomers in humans and dogs," *ISSX Proceedings, Fifth European ISSX Meeting*, Tours, France, Sep. 26-29, 1993, 1 page.

Package Insert: FDA Approved Labeling Text for NDA 20-717/S-005 &S-008, PROVIGIL® (modafinil) Tablets [C-IV], Jan. 23, 2004.

Aaltonen et al., "Solid form screening—A review," Euro. J. Pharmaceutics & Biopharmaceutics (2009), vol. 71, pp. 23-37.

Adams, Johnson, Wilcox, Laboratory Experiment in Organic Chemistry, 6th Ed. (1972), "Crsytallization and Sublimation".

Alvarez et al., "Polymorph Screening: Comparing a Semi-Automated Approach with a High Throughput Method," Crystal Growth & Design (2009), vol. 9, pp. 4181-4188.

Amidon et al., "A Theoretical Basis for a Biopharmaceutic Drug Classification: The Correlation of in Vitro Drug Product Dissolution and in Vivo Bioavailability," Pharma. Res. (1995), vol. 12, pp. 413-420.

Antonio, "4.2 EXAFS Extended X-Ray Absorption Fine Structure," Electron/X-Ray Diffraction (Encyclopedia of Materials Characterization (1992), pp. 214-226.

Approved Drug Products with Therapeutic Equivalence Evaluations, 29th Ed. (2009), ADA 15 of 179.

Arndt et al., "4.2. X-rays," Int'l Tables for Crystallography (2006), vol. C, Ch. 4.2, pp. 191-258.

Bearden, "X-ray Wavelengths," Rev. Modern Physics (1967), vol. 39, pp. 78-124.

Bernstein, "Ch. 14—Polymorphism and Patents from a Chemist's Point of View," Polymorphism in the Pharmaceutical Industry (2006), pp. 365-384.

Bernstein, "Crystal growth, polymorphism and structure—property relationships in organic crystals," J. Phys. D: Appl. Phys. (1993), vol. 26, pp. 866-876.

Bernstein, "Polymorphism—A Perspective", Crystal Growth & Design (2011), vol. 11, pp. 632-650.

Bernstein, "Concomitant Polymorphs", Angew. Chem. Int. Ed. (1999), vol. 38, pp. 3440-3461.

Bernstein, Polymorphism in Molecular Crystals book (2002), pp. 1-410.

Bernstein et al., "Disappearing and Reappearing Polymorphs—An Anathema to Crystal Engineering?" Crystal Engineering (1998), vol. 1, pp. 119-128.

Bernstein, "Chapter 13: Conformational Polymorphism," Organic Solid State Chemistry book, (1987); pp. 471-518.

Blomsma and Hilfiker (2003) Polymorphism & Crystallization Conference Abstracts in Brussels, Belgium.

Boylan et al., Handbook of Pharmaceutical Excipients (1st ed. 1986), pp. 3-4.

Brock et al., "On the Validity of Wallach's Rule: On the Density and Stability of Racemic Crystals Compared with Their Chiral Counterparts," J. Am. Chem. Soc. (1991), vol. 113, pp. 9811-9820.

Byrn et al., "Pharmaceutical Solids: A Strategic Approach to Regulatory Considerations," Pharmaceutical Research (1995), vol. 12, pp. 945-954.

Byrn et al., Solid-State Chemistry in Drugs (2d ed—1999), pp. 15-16; 259-260; 274-278.

Caira, "Crystalline Polymorphism of Organic Compounds," Topics in Current Chemistry (1998), vol. 198, pp. 163-208.

Carstensen et al., "Isoenergetic Polymorphs", Drug Dev. & Industrial Pharmacy (1995), vol. 21, pp. 523-536.

Chemburkar et al., "Dealing with the Impact of Ritonavir Polymorphs on the Late Stages of Bulk Drug Process Development," Organic Process Research & Development (2000), vol. 4, pp. 413-417.

Daeniker et al., "3-Quinuclidone Hydrochloride," Organic Syntheses (1973), Collective vol. 5, pp. 989-993.

Desiraju, "Crystal Gazing: Structure Prediction and Polymorphism," Science (1997), vol. 278, pp. 404-405.

Dunitz et al., "Disappearing Polymorphs," Acc. Chem. Res. (1995), vol. 28, pp. 193-200.

FDA "Guideline for Submitting Supporting Documentation in Drug Applications for the Manufacture of Drug Substances" (1987).

Federal Register (2000), vol. 65, No. 251, pp. 83041-83063.

Ferrari et al., "Solution-Mediated Transformation of α to β L-Glutamic Acid: Rate Enhancement Due to Secondary Nucleation," Crystal Growth & Design (2004), vol. 4, pp. 1061-1068.

Furniss, Vogel's textbook of Practical Organic Chemistry including Qualitative Organic Analysis (1978), pp. 106-108.

Furniss, Vogel's textbook of Practical Organic Chemistry (1989), pp. 32-34 and pp. 236-240.

Gardner et al., "Application of high throughput technologies to drug substance and drug product development," Computers and Chemical Engineering (2004), vol. 28, pp. 943-953.

Gavezzotti et al., "Polymorphic Forms of Organic Crystals at Room Conditions: Thermodynamic and Structural Implications," J. Am. Chem. Soc. (1995), vol. 117, pp. 12299-12305.

Gold et al., "Product Quality Research Initiative and Bulk Actives Post Approval Change," Drug Information Journal (1999), vol. 33, pp. 777-784.

Grant, "Theory and Origin of Polymorphism" Polymorphism in Pharmaceutical Solids book (1999), pp. 1-33.

Gu et al., "Polymorph Screening: Influence of Solvents on the Rate of Solvent-Mediated Polymorphic Transformation," J. Pharm. Sci. (2001), vol. 90, pp. 1878-1890.

Guidance for Industry ANDAs: Pharmaceutical Solid Polymorphism (2007), pp. 1-10.

Haleblian et al., "Pharmaceutical Applications of Polymorphorism," J. Pharm. Sci. (1969), vol. 58, pp. 911-929.

Henck et al., "Disappearing and Reappearing Polymorphs. The Benzocaine: Picric Acid System," J. Am. Chem. Soc. (2001), vol. 123, pp. 1834-1841.

Huang et al., "Glycine Exists Mainly as Monomers, Not Dimers, in Supersaturated Aqueous Solutions: Implications for Understanding its Crystallization and Polymorphism," J. Am. Chem. Soc. (2008), vol. 130, pp. 13973-13980.

(56) References Cited

OTHER PUBLICATIONS

Hursthouse et al., Why Do Organic Compounds Crystallise Well or Badly or Ever so Slowly? Why is Crystallisation Nevertheless Such a Good Purification Technique?, Organic Process Res. & Dev. (2009), vol. 13, pp. 1231-1240.

ICH Harmonised Tripartite Guideline Impurities: Guideline for Residual Solvents (1997), pp. 1-19.

ICH Harmonised Tripartite Guideline—Specifications: Test Procedures and Acceptance Criteria for New Drug Substances and New Drug Products: Chemical Substances Q6A (1999), pp. 1-46.

Jasinski et al., "Evaluation of the Abuse Liability of Modafinil and Other Drugs for Excessive Daytime Sleepiness Associated with Narcolepsy," Clinical Neuropharmacology (2000), vol. 23, pp. 149-156.

Jacques et al., Enantiomers, Racemates, and Resolutions (1981), pp. 130-147.

Jeffrey et al., "Three-Center (Bifurcated) Hydrogen Bonding in the Crystal Structures of Amino Acids," J. Am. Chem. Soc. (1984), vol. 106, pp. 5546-5553.

Jones, "Crystal Growing," Chemistry in Britain (1981), vol. 17, pp. 222-225.

Khankari et al., "Pharmaceutical hydrates," Thermochimica Acta (1995), vol. 248, pp. 61-79.

Kibbe, Handbook of Pharmaceutical Excipients (2000), Alcohol, pp. 7-9.

Kitaigorodskii—Organic Chemical Crystallography (1955), p. 103.

Lee et al., "Crystal Polymorphism in Chemical Process Development," Annu. Rev. Chem. Biomol. Eng. (2011), vol. 2, pp. 259-280.

Lorenz et al., "A contribution to the mandelic acid phase diagram," Thermochimica Acta (2004), vol. 415, pp. 55-61.

McConville, The Pilot Plant Real Book (2002), p. 6-44.

McCrone, "Ch. 8 Polymorphism," Physics and chemistry of the organic solid state (1965), pp. 725-767.

McCrone, Fusion Methods in Chemical Microscopy (1957), pp. 29-31.

Merck (The) Index, $10^{th}$ Ed. (1983), pp. 6, 34, 35.

Merck (The) Index, $10^{th}$ Ed. (1983), pp. 927, 483.

Morissette et al., "High-throughput crystallization: polymorphs, salts, co-crystals and solvates of pharmaceutical solids," Advanced Drug Delivery Review (2004), vol. 56, pp. 275-300.

Morissette et al., "Elucidation of crystal form diversity of the HIV protease inhibitor ritonavir by high-throughput crystallization," Proceedings of the Nat'l Academy of Sci. (2003), vol. 100, pp. 2180-2184.

Moulton et al., "From Molecules to Crystal Engineering: Supramolecular Isomerism and Polymorphism in Network Solids," Chem. Rev. (2001), vol. 101, pp. 1629-1658.

OECD Guideline for the Testing of Chemicals (1995), Melting Point / Melting Range, pp. 1-8.

Olmsted, Chemistry the Molecular Science (1994), pp. 148-149; 476-477.

Osorio-Lozada et al., "Synthesis and determination of the absolute stereochemistry of the enantiomers of adrafinil and modafinil", Tetrahedron: Asymmetry (2004), vol. 15, pp. 3811-3815.

Pauling, The Nature of the Chemical Bond and the Structure of Molecules and Crystals: An Introduction to Modern Structural Chemistry ($3^{rd}$ ed. (1960), Ch. 12, pp. 449-504.

Pavia, "Technique 3: Crystallization Purification of Solids," Introduction to Organic Laboratory Techniques 2d ed. (1982), pp. 481-491.

Pavia, Introduction to Organic Laboratory Techniques 3d ed. book (1976), pp. 522-532.

Pavia, Introduction to Organic Laboratory Techniques $1^{st}$ ed. book (1998), pp. 648-665.

Peterson et al., "Iterative High-Throughput Polymorphism Studies on Acetaminophen and an Experimentally Derived Structure for Form III," J. Am Chem. Soc. (2002), vol. 124, pp. 10958-10959.

Pimentel et al., The Hydrogen Bond, Chapter 1 (1960).

Pudipeddi et al., "Trends in Solubility of Polymorphs," J. Pharm. Sci. (2005), vol. 94, pp. 929-939.

Rafilovich et al., "Groth's Original Concomitant Polymorphs Revisited," Crystal Growth & Design (2005), vol. 5, pp. 2197-2209.

Rajopadhye et al., "Synthesis of Spiro[3H-indole-3,2'-tetrahydro-1,3-thiazine]-2,4'(1H)-diones," J. Heterocyclic Chem. (1985), vol. 22, p. 93.

Roberts et al., Basic Principles of Organic Chemistry (2d ed. 1977), pp. 607-612.

Rodriguez-Hornedo et al., "Significance of Controlling Crystallization Mechanisms and Kinetics in Pharmaceutical Systems," J. Pharmaceutical Sci. (1999), vol. 88, pp. 651-660.

Seddon et al., The Design and Application of Functional Solids (1999), pp. 20-25.

Stegemann et al., "When poor solubility becomes an issue: From early stage to proof of concept," Euro. J. Pharmaceutical Sci. (2007), vol. 31, pp. 249-261.

Stout et al., "Ch. 1—X-rays," X-Ray Structure Determination A Practical Guide (2d ed. 1989), pp. 7-17.

Thirunahari et al., Pharmaceutics, Preformation and Drug Delivery "Conformational Polymorphism of Tolbutamide: A Structural, Spectroscopic, and Thermodynamic Characterization of Burger's Forms I-IV," J. Pharm. Sci. (2010), vol. 99, pp. 2975-2990.

Threlfall, "Analysis of Organic Polymorphs a Review," Analyst (1995), vol. 120, pp. 2435-2460.

Toney, "Ch. 4—4.1—XRD—X-Ray Diffraction," Brundle Evans Wilson ed. Encyclopedia Materials Characterization (1992) pp. 198-213.

Tutton, "Ch. II—The Preparation and Selection of Measurable Crystals, and the Nature of the Process of Crystallisation from Solution," Crystallography and Practical Crystal Measurement (1964), pp. 10-31.

United States Pharmacopeia / The National Formulary (1985), USP 21; NF 16; pp. 22-23; 1281-1282; 1441-1517; 1530.

United States Pharmacopeia / The National Formulary (1995), USP 23; NF 18.

United States Pharmacopeia / The National Formulary (2000), USP 24; NF 19.

Van de Streek, "Searching the Cambridge Structural Database for Polymorphs," Acta Cryst. (2005), vol. B61, pp. 504-510.

Wade, Handbook of Pharmaceutical Excipients, 2d ed. (1994).

Webster's New World/Stedman's Concise Medical Dictionary (1987), pp. 21, 192.

Wiberg, Laboratory Technique in Organic Chemistry (1960), Chapter 5—The Reaction, pp. 191-245.

Wiberg, Laboratory Technique in Organic Chemistry (1960), pp. 98-104; 209-211.

Yates, "Ch. 12—Physical and Chemical Adsorption—Measurement of Solid Surface Areas," Physical and Magnetic Properties (1992), pp. 736-744.

Yu et al., "Physical characterization of polymorphic drugs: an integrated characterization strategy," Pharmaceutical Science & Technology Today (1998), vol. 1, pp. 118-127.

Evaporation Rates of Ethanol Solutions, Jan. 9, 2009 available at http://bayblab.blogspot.com/2009/01/evaporation-rates-of-ethanol-solutions.html.

Zallen, The Physics of Amorphous Solids, "12 The Formation of Amorphous Solids" (1983).

Zumdahl, "Ch. 10.3—An Introduction to Structures and Types of Solids," Chemistry (1986), pp. 390-393.

Avantium Life Sciences, Draft Technical Exhibit A to Master Research Services Agreement between Cephalon, Inc. and Avantium Technologies, BV, Dec. 17, 2003.

Beurier, J. Excerpt from Laboratory Notebook (1986), pp. 108-109, 111-112, 114, 116-118, 121.

Beurier, J. Excerpt from Laboratory Notebook (1986).

Smith (Exh. 5)—Handwritten list of synthetic steps (Feb. 2, 2012).

EPO Communication (PCT/FRO3/03799) dated Aug. 1, 2005.

Actavis ANDA Notice dated Oct. 30, 2009.

Apotex ANDA Notice dated Jul. 6, 2010.

Breckenridge Pharmaceutical, Inc. ANDA Notice dated Sep. 22, 2011.

Lupin Limited ANDA Notice dated Feb. 5, 2010.

Mylan Pharmaceuticals, Inc. ANDA Notice dated Nov. 2, 2009.

Sandoz Inc. ANDA Notice dated Jul. 27, 2011.

(56) References Cited

OTHER PUBLICATIONS

Sandoz Inc. ANDA Notice dated Dec. 15, 2009.
Teva Pharmaceuticals USA, Inc. ANDA Notice dated Oct. 19, 2009.
Watson Laboratories, Inc. ANDA Notice dated Nov. 24, 2009.
Apotex Inc. and Apotex Corp.'s Answering Claim Construction Brief, filed Jun. 15, 2011 (document 87).
Corrected Apotex Inc. and Apotex Corp.'s Opening Claim Construction Brief, filed Jun. 17, 2011 (document 101).
Corrected Apotex Inc. and Apotex Corp.'s Answering Claim Construction Brief, filed Jun. 17, 2011 (document 102).
Plaintiff's Opening Claim Construction Brief for US Patent No. 7,132,570, filed Jun. 1, 2011 (document 75).
Plaintiff's Answering Claim Construction Brief for US Patent No. 7,132,570, filed Jun. 15, 2011 (document 91).
Corrected Plaintiff's Opening Claim Construction Brief for US Patent No. 7,132,570, filed Jun. 17, 2011 (document 99).
Order Construing the Terms of US Patent No. 7,132,570, filed Jul. 25, 2011 (document 172).
Defendants' Opening Claim Construction Brief, filed Jun. 1, 2011 (document 77).
Defendants' Responsive Claim Construction Brief, filed Jun. 15, 2011 (document 90).
Corrected Defendants' Opening Claim Construction Brief, filed Jun. 16, 2011 (document 93).
Order filed Mar. 30, 2013 (document 329).
Defendants' Notice Pursuant to 35 USC §282 and Exhibit A dated Jun. 15, 2012.
Redacted Version of Exhibit M to the Joint Proposed Pretrial Order, filed Apr. 6, 2012 (document 268).
Corrected Proposed Findings of Fact and Conclusions of Law by Watson Laboratories, Inc., Sandoz Inc., Lupin Limited, and Apotex Inc., filed Nov. 7, 2012 (document 319).
Plaintiffs' Proposed Findings of Fact and Conclusions of Law, filed Oct. 17, 2012 (document 314).
Rebuttal Expert Report of Michael Cima, Ph.D. dated Dec. 20, 2011.
Opening Expert Report of Dr. Mark Hollingsworth dated Oct. 24, 2011.
Opening Expert Report of Dr. Michael J. Zaworotko dated Oct. 24, 2011.
Responsive Expert Report of Allan S. Myerson, Ph.D. dated Nov. 23, 2011.
Rebuttal Expert Report of Dr. Michael J. Zaworotko dated Dec. 20, 2011.
Responsive Expert Witness Report of Joel Bernstein, Ph.D. dated Nov. 23, 2011.
Brief of Defendant-Appellant Lupin Limited dated Jun. 28, 2013.
In et al., Crystal and Molecular Structure of (S)-(+)- and (R)-(−)-Enantiomers of Modafinil, a Novel Wake-Promoting Agent, Dec. 9, 2002.
Lavoix letter dtd Dec. 18, 2007 signed by Philippe Blot (L070501).
Exh. Mallamo 10 dtd Aug. 18, 2011 re 30(b)(6) Topics 10 and 11 from Notice 2.
Cephalon France et al., Int'l Prel. Exam. Report dtd Aug. 3, 2004 for PCT/FR2003/03799 application, filed Dec. 18, 2003.
Kress, M. Presentation on Development of Scalable Routes to Armodafinil: 2006 Albany Molecular Frontiers of Drug Discovery, Oct. 4-6, 2006.
Email from T. Carr to C. Besselievre & K. Smith dtd Aug. 25, 2005 re X-Ray of Modafinil Lots.
Presentation CEP-10953 R-modafinil (Polymorphism Screening) Review dtd Jul. 22, 2009.
Memo from R. McKean to C. Heacock, J. Mallmo, J. Turi dtd Sept 1, 2004 re DSC melting point of CEP-10953 as a function of scan rate.
Email from X. Wang to S. Rose dtd Sept 30, 2009 re NDA apparatus.
Laboratory Notebook pages regarding Experiment JB854 (May 22, 1986).
CRL40982: Ref 5/2173 Analysis (Sep. 25, 1989).
CRL40982 : Ref 5/2502 Analysis (Sep. 25, 1989).
Demande D'Analyse dtd Dec. 10, 2003.
Report from Crystallics BV to Cephalon Inc. re Crystallization of Racemic, (−) & (+) Modafinil (Mar. 2003).
Report from Cephalon France titled Analytical Development Report for Armodafinil (CEP-10953) Synthesis by Assymetric Oxidation (Oct. 25, 2005).
Graf, S. Development Report titled "Armodafinil by Asymmetric Oxidation Process" (May 24, 2005).
Email from L. Courvoisier to G. Coquerel regarding R-MDF (Spectres) (Jul. 20, 2009).
Orsymonde Report on 5 polymorphic forms of (−) modafinil and 2-solvates Mitry-Mory (Sep. 30, 2002).
Email from G. Coquerel to J. Mallamo regarding crystals for testing (Oct. 21, 2005).
Email from J. Mallamo to G. Martin regarding literature search (Apr. 28, 2006).
Report from Cephalon, Inc. titled "Process Development Report for the Manufacture of Armodafinil Drug Substance by Assymetric Oxidation" (Oct. 20, 2005).
Centre de Recherches L. Lafon Laboratoire de Chimie Analytique Data Table and Graph "Form I", (Sep. 25, 1989).
Centre de Recherches L. Lafon Laboratoire de Chimie Analytique Data Table and Graph "Entry 4; Compare w/Entry 6" (Sep. 25, 1989).
Email from S. Rose to G. Coquerel regarding Rapports IRCOF (Sep. 4, 2009).
Email from S. Rose to L. Courvoisier regarding Slides Sury + Brevet R-Modafinil (Jan. 29, 2007).
Email from S. Graf to L. Courvoisier re US Patent Issued 7317126 (Feb. 14, 2008).
Crystallics Exh. B: Technical Proposal CL001A, High ThroughPut Polymorph Screening Project (Dec. 9, 2002).
Cephalon, Inc. Master Laboratory Services Agmt. With Crystallics BV (Dec. 2, 2002).
Email from S. Field to X-P Wang re R-Modafinil—Form I (Nov. 18, 2003).
Memo from N. Claude to FC Lafon & C. Massare re Compte-rendu de la reunion du Apr. 19, 2000 regarding Faisabilite du developpement du CRL40982.
Memo from J. Beurier (Jun. 10, 1986).
Memo from C. Besselievre to Monsieur Frydman (Jul. 10, 2000) re Etude Polymorphique Du CRL40982.
Email from G. Serrure to J. Mallamo and S. Rose re Polymorphic results R-MDF vs S-MDF (Mar. 27, 2003).
Email from R. McKean to S. Rose re Preferred Crystallization Run (Jul. 19, 2004).
Email from E. Blomsma to R. McKean (Dec. 10, 2002).
Email from R. McKean to A. van Langevelde re PXRD of the racemate, R-isomer and S-isomer (Mar. 11, 2003).
Email from J. Mallamo to S. Rose re crystallics results (Apr. 23, 2003).
Email from N. Landmesser to G. Serrure re Polymorph information (Aug. 15, 2003).
Rapport Intermediaire 2 Etude 'Modafinil' 2, University De Rouen (Nov. 2000).
CEP10953 CMC Team Videoconference Meeting Summary (Jan. 29, 2004).
Presentation by Cephalon France Analytical Dept. (Jan. 18, 2005) re Armodafinil by Asymmetric Oxidation Analytical Review.
CRL40982 : Ref 5/2502 Analysis, Centre de Recherches L. Lafon Laboratoire de Chimie Analytique Data Table and Graph (Sep. 25, 1989).
Document re CRL4092 : Ref 5/2502 Analyse No. E36569 (Nov. 2, 1989).
Laboratoire L. Lafon's document regarding CRL40982, Analysis No. E36569 (Nov. 2, 1989).
Orsymonde—Note No. 02009—S. Rose to J. Mallamo and G. Serrure—Mitry-Mory (Sep. 30, 2002)—Report regarding (−) Modafinil Polymorph Forms, structural determination and Preparative Resolution of (+/−) Modafinic Acid (Modafinil acid derivative), (−) Modafinil (Coversheet) (Sep. 30, 2002).
Bingham et al., "Over one hundred solvates of sulfathiazole," *Chem. Commun.* (2001), pp. 603-604.

(56) References Cited

OTHER PUBLICATIONS

Desiraju, "Supramolecular Synthons in Crystal Engineering—A New Organic Synthesis," *Agnew. Chem. Int. Ed. Engl.* (1995), 34, pp. 2311-2327.
Desiraju, The C—H . . . O Hydrogen Bond in Crystals: What is it?, *Acc. Chem. Res.* (1991), 24, pp. 290-296.
Etter, "Hydrogen Bonds as Design Elements in Organic Chemistry," *J. Phys. Chem.* (1991), 95, pp. 4601-4610.
Etter, "Encoding and Decoding Hydrogen-Bond Patterns of Organic Compouds," *Acc. Chem. Res.* (1990), 23, pp. 120-126.
Amendment submitted in response to Final Office Action dated Mar. 11, 2005 w/RCE from Symyx Technologies to USPTO, filed Sep. 12, 2005.
Final Office Action dated Sep. 26, 2005 to Symyx Technologies from USPTO.
Fiese et al., "Preformulation", The Theory and Practice of Industrial Pharmacy (3d ed. 1976), pp. 171-196.

* cited by examiner

FIG.11  FORM IV

FIG. 13 ACETONITRILE SOLVATE

PROCESS FOR THE PREPARATION OF AND CRYSTALLINE FORMS OF OPTICAL ENANTIOMERS OF MODAFINIL

CROSS REFERENCE TO RELATED APPLICATIONS

This application is a continuation of U.S. application Ser. No. 13/858,483, filed Apr. 8, 2013, which is a continuation U.S. application Ser. No. 12/507,631, filed Jul. 22, 2009, which is a divisional of U.S. application Ser. No. 11/474,859, filed Jun. 26, 2006, which is a continuation of U.S. application Ser. No. 10/539,918 (U.S. Pat. No. 7,132,570, issued Nov. 7, 2006), which was the National Stage of PCT/FR2003/003799, filed Dec. 18, 2003, which claims priority to French Application No. 0216412, filed Dec. 20, 2002. The foregoing applications are incorporated herein by reference in their entireties, for all purposes.

FIELD OF THE INVENTION

The invention relates to a process for obtaining crystalline forms of the enantiomers of modafinil, and the crystalline forms which it is possible to obtain according to this process.

The invention also relates to a new process for the preparation of optical enantiomers of modafinil from (±) modafinil acid.

BACKGROUND OF THE INVENTION

U.S. Pat. No. 4,177,290 describes modafinil in racemic form, also known as (±) 2-(benzhydrylsulphinyl)acetamide or (±) 2-[(di-phenylmethyl)sulphinyl]acetamide, as a compound having properties of stimulating the central nervous system.

U.S. Pat. No. 4,927,855 describes the two optical enantiomers of modafinil. More particularly it describes the laevorotatory enantiomer and its use as an antidepressant or stimulant agent in the treatment of hypersomnia and disorders associated with Alzheimer's disease. The process for the preparation of the two optical enantiomers of modafinil from (±) modafinil acid or (±)-benzhydrylsulphinylacetic acid described in this document is illustrated in the following synthesis diagram:

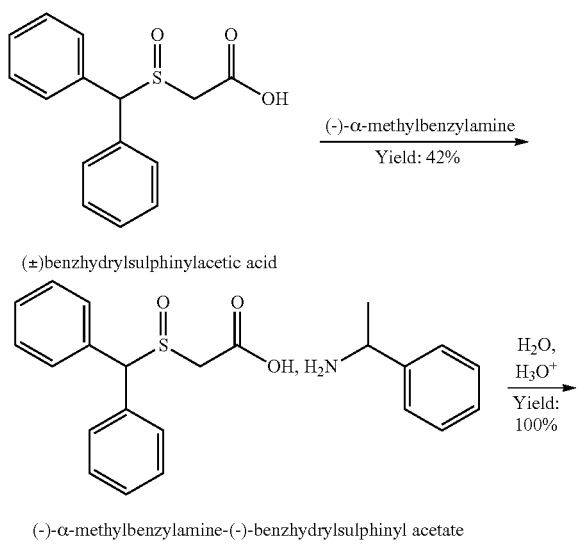

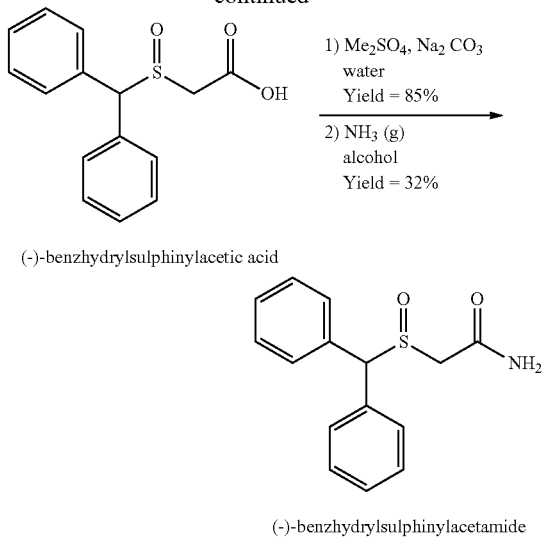

*In relation to (-)-benzhydrylsulphinylacetic acid

This process comprises carrying out resolution of the optical enantiomers of (±) modafinil acid in a first stage via the formation of diastereoisomers with the optically active agent α-methylbenzylamine.

The (−)-α-methylbenzylamine-(−)-benzhydrylsulphinyl acetate is then converted to (−)-benzhydrylsulphinylacetic acid by acid hydrolysis. The latter is esterified in the presence of dimethyl sulphate and then converted to amide in the presence of ammonia (gas). The (−) or l (laevorotatory) enantiomer of modafinil is obtained through this process with an overall yield of 5.7% in relation to the (±) modafinil acid, calculated on the basis of the yields corresponding to each stage.

SUMMARY OF THE INVENTION

The term "enantiomer" refers to stereoisomer molecules which are non-superimposable mirror images of each other. Enantiomers are typically designated using either (+) and (−) or (d) and (l), which indicates optical rotating power in the chiral centre.

Stereoisomerism may also be denoted by either (D) or (L) or by (R) and (S), these being descriptive of the absolute configuration.

In what follows the laevorotatory enantiomer of modafinil will be referred to without distinction as the l or (−) enantiomer, and the dextrorotatory enantiomer will for its part be referred to as the d or (+) enantiomer.

A process through which different crystalline forms of the optical enantiomers of modafinil can be obtained has now been discovered. More specifically the inventors have shown that the crystalline form obtained mainly depends on the nature of the crystallisation solvent used.

For the purposes of this description the term "crystalline form" refers to either a polymorphic form or a solvate, without distinction.

By "polymorphic form" is meant an organised structure involving only molecules of the solute, having a characteristic crystalline signature.

The term "solvate" relates to an organised structure having a characteristic crystalline signature which involves both molecules of solute and molecules of solvent. Solvates having one molecule of solute for one molecule of solvent are called true solvates.

Furthermore the inventors have shown that l-modafinil and d-modafinil prepared according to the conditions described in U.S. Pat. No. 4,177,290 are obtained in the form of one polymorphic form described as form I, which corresponds to the thermodynamically most stable polymorphic form under normal temperature and pressure conditions.

Form I has the X-ray diffraction spectrum below in which d represents the interplanar spacing and the ratio (I/Io) the relative intensity.

| CRL 40982 FORM I | | |
|---|---|---|
| 2 Theta (degrees) | d (Å) | I/Io (%) |
| 9.8 | 13.40 | 32 |
| 15.4 | 8.54 | 87 |
| 20.8 | 6.34 | 24 |
| 26.4 | 5.01 | 14 |
| 28.3 | 4.68 | 19 |
| 28.7 | 4.62 | 16 |
| 29.9 | 4.44 | 45 |
| 31.1 | 4.27 | 100 |
| 31.6 | 4.20 | 23 |
| 32 | 4.15 | 14 |
| 33.1 | 4.02 | 78 |
| 33.4 | 3.98 | 84 |
| 34.1 | 3.90 | 16 |
| 35.1 | 3.80 | 15 |
| 39 | 3.43 | 22 |

Diffractometer: Miniflex Rigaku (Elexience)

The crystalline forms of a given compound generally have physical, pharmaceutical, physiological and biological properties which differ from each other very sharply.

In this respect the crystalline forms of optically active modafinil, in particular the polymorphic forms, are of interest in that they have different and advantageous properties in comparison with form I.

According to another aspect, a new process for the preparation of the optical enantiomers of modafinil from (±)-modafinil acid has now been discovered, and this process can be used to isolate each enantiomer in yields and with an optical purity which are markedly superior to those described in U.S. Pat. No. 4,927,855.

In a particularly advantageous fashion a process for resolution of the two optical enantiomers of (±)-modafinil acid by preferential crystallisation, which is advantageously applicable to the preparation scale, has now been developed.

This process for the resolution of (±)-modafinil acid has many advantages:

it avoids the use of a costly chiral intermediate whose further preparation involves losses which are rarely less than 10% (De Min., M., Levy, G. and Michwater J.-C., 1988, J. Chem. Phys. 85, 603-19), the two enantiomers are obtained directly, contrary to the method which makes use of conventional resolution through the formation of diastereoisomer salts, the yield is theoretically quantitative as a result of successive recycling of the mother liquors, Purification of the crude enantiomer crystals is easy.

The invention therefore aims to provide a process of preparation for crystalline forms of the enantiomers of modafinil.

The invention also aims to provide a new process for preparation of the optical enantiomers of modafinil, and in particular the laevorotatory enantiomer of modafinil.

DETAILED DESCRIPTION OF THE INVENTION

Process for the Preparation of l-Modafinil Polymorphs

These objects and others are accomplished by this invention which relates more particularly, in a first aspect, to a process for the preparation of crystalline forms of the optical enantiomers of modafinil, comprising the following stages:

i) dissolving one of the optical enantiomers of modafinil in a solvent other than ethanol, ii) crystallising the said enantiomer of modafinil, and iii) recovering the crystalline form of the said enantiomer of modafinil so obtained.

For the purposes of this invention, the solvent used in stage i) of the process, also referred to as the "recrystallisation solvent", is a solvent capable of bringing about crystallisation of the said optical enantiomer of modafinil, preferably at atmospheric pressure. In other words it comprises any solvent A which with at least one of the enantiomers is capable of forming at a given pressure in a first temperature and concentration domain, a monophase system comprising at least one of the enantiomers in dilute solution in solvent A, in a second temperature and concentration domain which is not the same as the former, a second two-phase system comprising crystals of the said enantiomer in the presence of saturated solution, the two domains being separated from each other by the solubility curve of the said enantiomer T (° C.)=f (enantiomer concentration) at the pressure considered.

In general the crystallisation in stage ii) comprises changing from the monophase system to the two-phase system by varying the temperature and concentration.

By way of a non-restrictive illustration of solvents which may be suitable for the recrystallisation process according to the invention mention may in particular be made of alcoholic solvents, carboxylic acid ester solvents, ether solvents, chlorinated solvents, aromatic solvents, and lower aliphatic ketone solvents. Other solvents are for example, carboxylic acid solvents, aprotic polar solvents, alicyclic hydrocarbons, aliphatic hydrocarbons, carbonates, heteroaromatics and water.

Among the alcoholic solvents mention may be made in particular of lower alkyl alcohols such as methanol, ethanol, propanol, isopropanol, butanol, isobutanol, 2-methyl-2-pentanol, 1,2-propanediol and t-amyl alcohol, with methanol, propanol and isopropanol being particularly preferred.

Among solvents of the carboxylic acid ester type mention may be made in particular of alkyl acetates such as methyl acetate, ethyl acetate, n-propyl acetate, isopropyl acetate, n-butyl acetate and alkyl formates such as ethyl formate, with ethyl acetate being particularly preferred.

Useful ether recrystallisation solvents are diethylether, tetrahydrofuran (THF), dioxan, dibutylether, isopropyl ether, t-butylmethylether and tetrahydropyran, with tetrahydrofuran being particularly preferred.

Among the chlorinated solvents mention may be made of chlorinated hydrocarbons, in particular chloroform, 1,2-dichloroethane, dichloromethane and chlorinated aromatics such as chlorobenzene.

As examples of aromatic solvents mention may be made of ortho, meta, and para xylene or a mixture of ortho, meta and para xylene, methoxybenzene, nitrobenzene, trifluorotoluene and toluene, with ortho, meta and para xylene being particularly preferred.

Useful ketone solvents are solvents such as acetone, methylethylketone, methylisobutylketone, butan-2-one, cyclopentanone, isobutylmethylketone, 2-pentanone, 3-pentanone.

As an example of a carboxylic acid solvent, mention may be made in particular of acetic acid.

By way of an example of a heteroaromatic solvent, mention may be made in particular of pyridine.

Examples of aprotic polar solvents are in particular acetonitrile, propionitrile, 4-methylmorpholine, N,N-dimethylacetamide, nitromethane, triethylamine, N-methyl-pyrrolidone (NMP).

Examples of aliphatic hydrocarbons are in particular heptane, 2,2,4-trimethyl pentane.

Examples of alicyclic hydrocarbons are in particular cyclopentane, cyclohexane.

Examples of carbonates are in particular alkyl carbonates such as dimethyl carbonate.

According to a preferred embodiment of the process according to the invention the crystallisation solvents are selected from acetone, methanol, 1-4 dioxan, ethyl acetate, mixtures of ortho, meta, para xylene, isopropanol, n-propanol, dimethyl carbonate, tetrahydrofuran, chloroform and methylethylketone, water and alcohol/$H_2O$ mixtures.

Thus, crystalline forms of the optical enantiomers of modafinil can be obtained by recrystallisation of the enantiomers in particular solvents, where the nature and possibly the conditions of crystallisation mainly determine the type of crystalline form obtained.

Through its interaction with functional groups and electron-attracting or electron-donor substituents the recrystallisation solvent can in fact encourage certain molecular arrangements which give rise to a particular crystalline form under given crystallisation conditions.

Generally the recrystallisation solvent used in stage i) is heated, in particular under reflux, until the optical enantiomer of modafinil is completely dissolved in the solvent. Although the concentration of the optical enantiomer of modafinil in stage i) is not a critical factor for the crystallisation, it is however preferable to work in the presence of a concentration of optical enantiomer of modafinil which is close to the saturation concentration in the recrystallisation solvent in question.

According to one embodiment the optical enantiomer of modafinil is dissolved by heating the solvent under reflux and an additional quantity of the said optical enantiomer is then added in fractions in such a way as to achieve saturation. Additional solvent may be added to ensure complete dissolution.

According to another embodiment the optical enantiomer of modafinil is suspended in the solvent heated under reflux and an additional quantity of solvent is then added in fractions so as to obtain a homogeneous solution and thus achieve saturation.

The process of crystallisation of the optical enantiomer of modafinil in stage ii) may be accelerated using techniques known to those skilled in the art, namely cooling of the solution, evaporation of some of the solvent, the addition of an antisolvent or seeding the solution with crystals of optically active modafinil having the same crystalline form as that desired. Most commonly the mixture is stirred continually throughout the crystallisation process so as to obtain a homogeneous suspension and rapid renewal of the mother liquor around each crystallite.

The crystallisation process in the process according to the invention may be carried out under thermodynamic or kinetic conditions.

For the purposes of this description, by "crystallisation under thermodynamic conditions" is meant crystallisation performed under conditions in which equilibrium is maintained between the homogeneous solution and the saturated solution in the presence of crystals of l- or d-modafinil.

By way of example, a thermodynamic crystallisation may be performed by slowly cooling the solution obtained in stage i), typically by allowing the solution to cool to ambient temperature or by applying a rate of cooling or a cooling gradient which is preferably less than or equal to 0.75° C./min, more preferably to 0.6° C./min and more preferably to 0.5° C./min.

By "crystallisation performed under kinetic conditions" for the purposes of this description is meant a crystallisation in which equilibrium between the homogeneous solution and the saturated solution in the presence of crystals of d- or l-modafinil is suddenly displaced towards the latter two-phase domain, i.e. towards the formation of crystals.

By way of illustration, a crystallisation which is said to be kinetic can be performed in particular by rapid cooling, for example by implementing a cooling gradient of 300° C./min, or by precipitation through the addition of an antisolvent to the solution obtained in stage i).

By way of an illustrative and non-restrictive example these two types of thermodynamic or kinetic crystallisation are effected in this description by slow or rapid cooling.

Of course any other technique of crystallisation such as evaporation of the solvent or precipitation which would make it possible for kinetic and/or thermodynamic conditions to obtain also falls within the scope of the process according to the invention.

Thus according to a particular embodiment the crystallisation in stage ii) may be performed by precipitation, possibly in the presence of seed crystals of the desired crystal form.

The inventors have also shown that some solvents can give rise to different crystalline forms, more specifically to polymorphic forms, according to whether the crystallisation is performed under kinetic or thermodynamic conditions.

According to a particularly advantageous embodiment crystallisation comprises cooling of the solution obtained in stage i).

As applicable, in a first mode, cooling is rapid and generally corresponds to quenching of the solution obtained in stage i) in a bath at a temperature at or below 0° C. such as a bath of ice water for a sufficient time to permit complete crystallisation of the solution, or again cooling with a temperature gradient of for example between −1° C. and −5° C./min.

According to a second embodiment cooling is slow. In this context the solution is generally allowed to cool from the reflux temperature of the solvent to ambient temperature or the solution is cooled with a cooling gradient preferably between −0.1° C./min and −0.8° C./min, and more preferably close to −0.5° C./min, generally down to a temperature of 15° to 20° C.

Among the preferred combinations of solvents/antisolvents according to the invention mention may be made in particular of the combinations water/acetone, acetonitrile/water, ethanol/water, methanol/water, acetic acid/water.

Finally the crystalline forms of the optical enantiomers of modafinil can be isolated using conventional methods such as filtration and centrifuging.

By way of a non-restrictive illustration the process of preparation according to the invention is more particularly implemented using the laevorotatory enantiomer of modafinil.

According to a particular embodiment the crystalline form obtained according to this process is a polymorphic form.

In this respect it will be noted that in general each of the (l) and (d) enantiomers of a given chemical compound yield crystalline forms, in particular polymorphic forms, having powder X-ray diffraction spectra which are identical when they are recrystallised under the same experimental conditions.

In this respect reference should be made in particular to the work of J. Bernstein <<Polymorphism in molecular crystals>> 2002, University Press, Oxford, UK, and the publication by G. Coquerel, Enantiomer, 2000; 5(5): 481-498, Gordon and Breach Science Publishers.

In this respect the dextrorotatory form, whose X-ray diffraction spectra for the crystalline forms are identical to those of the laevorotatory form described below and vice versa, forms part of the invention.

In what follows the polymorphic forms designated forms I, II, III, IV and V also cover the CRL 40982 forms I, II, III, IV, V obtained from the laevorotatory enantiomer and the CRL 40983 forms I, II, III, IV, V obtained from the dextrorotatory enantiomer.

Form I

In this context, the process using a solvent selected from acetone, ethanol, 1-4 dioxan, ethyl acetate and mixtures of ortho, meta and para xylene, and a stage of crystallisation by slow cooling leads to the acquisition of form I or CRL 40982 form I.

The process using a solvent selected from methanol, water or alcohol/water mixtures, in particular methanol/water and ethanol/water, and a stage of crystallisation by rapid cooling leads to the acquisition of form I or CRL 40982 form I.

According to another equally preferred variant of the invention, the process using methanol and a stage of crystallisation by precipitation through the addition of cold water as an antisolvent for methanol leads to form I.

Form II

According to another embodiment of the invention, the process using a solvent in stage i) selected from isopropanol, ethyl acetate, n-propanol, or ethanol denatured with toluene and a stage of crystallisation by rapid cooling leads to a polymorphic form described as Form II or CRL 40982 form II.

According to a variant of the process form II can also be obtained by slow cooling from isopropanol.

It may also be commented that the production of form II from isopropanol does not depend on the conditions of crystallisation (thermodynamic or kinetic).

Form III

According to another variant of the process according to the invention the solvent used in stage i) is acetone, and crystallisation stage ii) comprises rapid cooling, this apparently leading to acquisition of a polymorphic form described as form III or CRL 40982 form III.

Form IV

As a variant of the process according to the invention, the solvent used in stage i) is selected from tetrahydrofuran, chloroform and methylethylketone, and crystallisation stage ii) comprises slow cooling of the solution, as a result of which a polymorphic form described as form IV or CRL 40982 form IV is obtained.

Depending upon the nature of the solvent used, the process for recrystallisation of the optical enantiomers of modafinil can give rise to the production of solvates.

Form V

As a variant of the process according to the invention the solvent used in stage i) is selected from 2-pentanone and tetrahydrofuran, and crystallisation stage ii) comprises slow cooling of the solution in 2-pentanone and rapid cooling in THF, as a result of which a polymorphic form described as form V is obtained.

Dimethyl Carbonate Solvate

Thus according to a particular embodiment of the invention, when the solvent used in stage i) is dimethyl carbonate and crystallisation consists of slow cooling, a dimethyl carbonate (−)-modafinil solvate is obtained.

Acetic Acid Solvate

According to a particular embodiment of the invention, when the solvent used in stage i) is acetic acid and crystallisation consists of a rapid or slow cooling, an acetic acid solvate is obtained.

Polymorphic Forms of (−)-Modafinil

The invention also relates to the polymorphic form of the laevorotatory enantiomer of modafinil described as CRL 40982 form II, characterised in that it produces an X-ray diffraction spectrum comprising intensity peaks for the interplanar spacings: 11.33, 8.54, 7.57, 7.44, 4.56, 3.78, 3.71 Å, the intensity peaks corresponding to the interplanar spacings of 8.54, 7.57, 7.44, 4.56, 3.78, 3.71 Å being particularly characteristic.

More specifically the X-ray diffraction spectrum below, in which d represents the interplanar spacing and I/Io the relative intensity:

| CRL 40982 FORM II | | |
| --- | --- | --- |
| 2 Theta (degrees) | d (Å) | I/Io (%) |
| 11.6 | 11.33 | 54 |
| 15.4 | 8.54 | 58 |
| 17.4 | 7.57 | 41 |
| 17.7 | 7.44 | 34 |
| 23.3 | 5.67 | 19 |
| 24.8 | 5.33 | 26 |
| 27.4 | 4.83 | 19 |
| 28.9 | 4.59 | 36 |
| 29.1 | 4.56 | 97 |
| 29.8 | 4.45 | 23 |
| 32.8 | 4.05 | 29 |
| 34.3 | 3.88 | 23 |
| 35.3 | 3.78 | 100 |
| 35.9 | 3.71 | 40 |
| 40.1 | 3.34 | 21 |
| 47.7 | 2.83 | 20 |
| 53.7 | 2.53 | 32 |

Diffractometer: Miniflex Rigaku (Elexience)

The invention also relates to the polymorphic form of the laevorotatory enantiomer of modafinil described as CRL 40982 form III, characterised by an X-ray diffraction spectrum incorporating intensity peaks at the following interplanar spacings d: 13.40, 12.28, 8.54, 7.32, 6.17, 5.01, 4.10, 3.97, 3.42, 3.20 Å, and the interplanar spacings: 12.28, 8.54, 5.01, 4.10, 3.97, 3.42, 3.20 Å corresponding to the most characteristic intensity peaks.

In this context the invention relates more particularly to form III of (−)-modafinil which produces the following X-ray diffraction spectrum in which d represents the interplanar spacing and I/Io the relative intensity:

| CRL 40982 FORM III | | |
| --- | --- | --- |
| 2 Theta (degrees) | d (Å) | I/Io (%) |
| 9.8 | 13.40 | 40 |
| 10.7 | 12.28 | 39 |
| 15.4 | 8.54 | 100 |
| 18.0 | 7.32 | 33 |
| 21.4 | 6.17 | 23 |
| 25.9 | 5.11 | 26 |
| 26.4 | 5.01 | 87 |

-continued

| CRL 40982 FORM III | | |
|---|---|---|
| 2 Theta (degrees) | d (Å) | I/Io (%) |
| 29.6 | 4.48 | 26 |
| 29.9 | 4.44 | 20 |
| 31.1 | 4.27 | 34 |
| 31.7 | 4.19 | 20 |
| 32.4 | 4.10 | 77 |
| 33.1 | 4.02 | 23 |
| 33.5 | 3.97 | 64 |
| 36.5 | 3.66 | 38 |
| 39.1 | 3.42 | 40 |
| 41.9 | 3.20 | 32 |
| 46.4 | 2.91 | 23 |
| 52.7 | 2.58 | 25 |

Diffractometer: Miniflex Rigaku (Elexience)

The invention also relates to the polymorphic form of the laevorotatory enantiomer of modafinil described as CRL 40982 form IV, characterised in that it produces an X-ray diffraction spectrum comprising intensity peaks at the interplanar spacings: 12.38; 8.58; 7.34; 6.16; 5.00; 4.48; 4.09; 3.66 Å, the most characteristic peaks corresponding to the interplanar spacings of 12.38; 8.58; 7.34; 5.00; 4.09 Å.

More specifically, form IV of (−)-modafinil is characterised in that it produces the following X-ray diffraction spectrum in which d represents the interplanar spacing and I/Io the relative intensity comprising intensity peaks at the interplanar spacings:

| CRL 40982 FORM IV | | |
|---|---|---|
| 2 Theta (degrees) | d (Å) | I/Io (%) |
| 6.37 | 13.88 | 26 |
| 7.14 | 12.38 | 69 |
| 8.60 | 10.27 | 23 |
| 10.30 | 8.58 | 100 |
| 12.04 | 7.34 | 49 |
| 14.37 | 6.16 | 24 |
| 15.65 | 5.66 | 11 |
| 17.30 | 5.12 | 29 |
| 17.72 | 5.00 | 60 |
| 19.12 | 4.64 | 15 |
| 19.81 | 4.48 | 25 |
| 20.82 | 4.26 | 10 |
| 21.24 | 4.18 | 12 |
| 21.70 | 4.09 | 51 |
| 23.28 | 3.82 | 9 |
| 24.30 | 3.66 | 30 |
| 25.18 | 3.53 | 9 |
| 26.02 | 3.42 | 21 |
| 27.13 | 3.28 | 9 |
| 27.90 | 3.20 | 15 |

Diffractometer: Siemens AG.

The invention also relates to the polymorphic form of the dextrorotatory enantiomer of modafinil referred to as CRL 40983 form V, characterised in that it produces an X-ray diffraction spectrum comprising intensity peaks at the interplanar spacings 9.63, 5.23; 5.03, 4.74, 4.66, 4.22, 4.10, 3.77 (Å).

| CRL 40983 FORM V | | |
|---|---|---|
| 2 Theta (degrees) | d (Å) | I/Io (%) |
| 6.65 | 13.27 | 22 |
| 7.24 | 12.21 | 5 |

-continued

| CRL 40983 FORM V | | |
|---|---|---|
| 2 Theta (degrees) | d (Å) | I/Io (%) |
| 9.17 | 9.63 | 51 |
| 10.38 | 8.51 | 19 |
| 12.28 | 7.20 | 15 |
| 14.33 | 6.17 | 14 |
| 15.81 | 5.60 | 4 |
| 16.95 | 5.23 | 68 |
| 17.64 | 5.03 | 100 |
| 18.69 | 4.74 | 51 |
| 19.03 | 4.66 | 58 |
| 20.06 | 4.42 | 3 |
| 21.06 | 4.22 | 91 |
| 21.67 | 4.10 | 64 |
| 22.39 | 3.97 | 17 |
| 23.61 | 3.77 | 55 |
| 24.64 | 3.61 | 8 |
| 25.40 | 3.50 | 13 |
| 26.21 | 3.40 | 20 |
| 26.95 | 3.31 | 18 |

Diffractometer: Bruker GADDS

The invention also relates to the dimethyl carbonate solvate of (−)-modafinil, characterised by the following diffraction spectrum in which d represents the interplanar spacing and I/Io the relative intensity:

| DIMETHYL CARBONATE SOLVATE | | |
|---|---|---|
| 2 Theta (degrees) | d (Å) | I/Io (%) |
| 7.17 | 12.31 | 38 |
| 9.12 | 9.69 | 29 |
| 9.72 | 9.09 | 16 |
| 10.35 | 8.54 | 35 |
| 12.17 | 7.27 | 100 |
| 14.25 | 6.21 | 16 |
| 16.26 | 5.45 | 10 |
| 17.36 | 5.10 | 13 |
| 17.72 | 5.00 | 21 |
| 18.35 | 4.83 | 9 |
| 19.16 | 4.63 | 9 |
| 19.88 | 4.46 | 14 |
| 21.04 | 4.22 | 12 |
| 21.49 | 4.13 | 25 |
| 21.73 | 4.09 | 24 |
| 23.49 | 3.78 | 22 |
| 24.55 | 3.62 | 35 |
| 25.24 | 3.53 | 8 |
| 26.05 | 3.42 | 9 |
| 26.88 | 3.32 | 7 |
| 27.48 | 3.24 | 13 |
| 27.81 | 3.21 | 10 |
| 28.79 | 3.10 | 8 |

Diffractometer: Siemens AG.

The invention also relates to the acetic acid solvate of the laevorotatory and dextrorotatory enantiomers of modafinil which can be obtained by the recrystallisation process according to the invention, characterised in that it produces a X-ray diffraction spectrum comprising intensity peaks at the interplanar spacings: 9.45; 7.15; 5.13; 4.15; 3.67 (Å).

| ACETIC ACID SOLVATE | | |
|---|---|---|
| 2-Theta (degrees) | d (Å) | I/Io % |
| 6.64 | 13.30 | 8.5 |
| 7.15 | 12.35 | 15 |
| 9.36 | 9.45 | 100 |

| ACETIC ACID SOLVATE | | |
|---|---|---|
| 2-Theta (degrees) | d (Å) | I/Io % |
| 10.43 | 8.48 | 6.5 |
| 12.38 | 7.15 | 25 |
| 14.38 | 6.16 | 15 |
| 16.37 | 5.41 | 8 |
| 17.29 | 5.13 | 28 |
| 17.82 | 4.97 | 21 |
| 18.24 | 4.86 | 16 |
| 18.96 | 4.68 | 7 |
| 19.24 | 4.61 | 6 |
| 20.09 | 4.42 | 20 |
| 21.40 | 4.15 | 75 |
| 22.55 | 3.94 | 21 |
| 23.42 | 3.80 | 7 |
| 24.25 | 3.67 | 40 |
| 24.92 | 3.57 | 12 |
| 25.21 | 3.53 | 9.5 |
| 26.15 | 3.40 | 11 |
| 26.78 | 3.33 | 8 |
| 26.99 | 3.30 | 6 |
| 28.43 | 3.14 | 13 |
| 28.79 | 3.10 | 14 |
| 29.63 | 3.01 | 7 |
| 30.03 | 2.97 | 4 |
| 32.33 | 2.77 | 9 |
| 33.13 | 2.70 | 7 |
| 34.29 | 2.61 | 3 |
| 34.86 | 2.57 | 7 |
| 35.90 | 2.50 | 7 |

Diffractomètre: Bruker GADDS

According to another aspect, the invention also relates to a process for conversion from a first crystalline form of one of the enantiomers of modafinil to a second crystalline form which is different from the former, the said process comprising the stages of:

i) suspending the crystalline form of the said enantiomer of modafinil in a solvent;

ii) recovering the crystalline form obtained.

By way of solvents which may be suitable for this process mention may be made in particular of acetonitrile.

In general the initial crystalline form is held in suspension at a temperature lower than the homogenisation temperature for a sufficient length of time to permit total conversion of the initial form. This period may vary in particular according to the nature of the solvent, the initial crystalline form and the temperature of the medium. Conventionally the crystalline form is held in suspension for at least 24 hours at ambient temperature under atmospheric pressure, most commonly for approximately 72 hours.

By way of illustration this process is implemented using (−)-modafinil.

In this context, according to a particular embodiment of the invention, the process uses form I in acetonitrile in stage i), as a result of which an acetonitrile solvate of (−)-modafinil is obtained.

By way of indication form I is held in suspension for several days, preferably for 3 days at ambient temperature, at atmospheric pressure.

The invention also relates to the acetonitrile solute of (−)-modafinil which can be obtained through the recrystallisation process according to the invention. It is characterised by the following diffraction spectrum in which d represents the interplanar spacing and I/Io the relative intensity:

| ACETONITRILE SOLVATE | | |
|---|---|---|
| 2 Theta (degrees) | d (Å) | I/Io (%) |
| 5.46 | 16.17 | 46 |
| 6.25 | 14.14 | 95 |
| 7.17 | 12.32 | 51 |
| 8.28 | 10.66 | 81 |
| 9.02 | 9.79 | 68 |
| 9.51 | 9.29 | 53 |
| 10.34 | 8.54 | 53 |
| 10.84 | 8.15 | 63 |
| 11.33 | 7.80 | 79 |
| 12.47 | 7.09 | 53 |
| 14.02 | 6.31 | 45 |
| 15.20 | 5.83 | 35 |
| 15.76 | 5.62 | 34 |
| 16.37 | 5.41 | 40 |
| 17.37 | 5.10 | 51 |
| 18.10 | 4.90 | 46 |
| 19.05 | 4.66 | 44 |
| 19.36 | 4.58 | 37 |
| 19.89 | 4.46 | 39 |
| 20.48 | 4.33 | 59 |
| 21.14 | 4.20 | 55 |
| 22.10 | 4.02 | 100 |
| 22.65 | 3.92 | 60 |
| 23.17 | 3.835 | 42 |
| 23.89 | 3.72 | 33 |
| 24.72 | 3.60 | 38 |
| 24.93 | 3.57 | 37 |
| 25.81 | 3.45 | 37 |
| 26.73 | 3.33 | 55 |
| 27.52 | 3.24 | 30 |
| 27.97 | 3.19 | 30 |
| 28.89 | 3.09 | 31 |
| 29.44 | 3.03 | 27 |

Diffractometer: Siemens AG.

Pharmaceutical Compositions Comprising Polymorphic Forms II, III, IV and V of (−)-Modafinil and (+)-Modafinil Respectively The invention also relates to pharmaceutical compositions comprising the polymorphic forms CRL 40982 form II, CRL 40982 form III, CRL 40982 form IV or CRL 40982 form V of (−)-modafinil and form CRL 40983 form II, CRL 40983 form III, CRL 40983 form IV and CRL 40983 form V respectively, possibly in association with a pharmaceutically acceptable vehicle.

These compositions may be administered orally, via the mucosa (for example, the mucosa of the eye, nose, lungs, stomach, intestines, rectum, vagina or the urinary apparatus) or parenterally (for example subcutaneously, intradermally, intramuscularly, intravenously or intraperitoneally).

According to a preferred embodiment the pharmaceutical compositions according to the invention are administered orally in the form of tablets, pills, gelules or immediate release or controlled release granules, in the form of powder, capsules, suspension of a liquid or in a gel or emulsion, or as a lyophilisate, or preferably in the form of tablets, capsules, suspension in a liquid or in a gel. The vehicle for administration may comprise one or more pharmaceutically acceptable excipients which are likely to ensure stability of the polymorphic forms (for example a suspension of a polymorph in an oil).

The pharmaceutical compositions according to the invention comprise the II, III, IV or V polymorphic forms of (−)-modafinil and (+)-modafinil respectively, possibly as mixtures of each other and/or with one or more pharmaceutically acceptable excipients.

A solid composition for oral administration is prepared by adding one or more excipients to the active ingredient, in particular a filler, and, if appropriate a binder, an exfoliating agent, a lubricant, a surfactant and an emulsifier, a solubiliser, a colouring agent, a sugar substitute or a taste modifier, with the mixture being formed for example into the form of a table or capsule.

Examples of fillers include lactose, sucrose, mannitol or sorbitol; preparations based on cellulose, such as for example maize starch, rice starch, potato starch.

Examples of binders include gelatine, gum tragacanth, methylcellulose, hydroxypropylcellulose, sodium carboxymethylcellulose, and/or polyvinyl pyrrolidone (PVP), povidone, copovidone, dextran, dextrin, cyclodextrin and its derivatives such as hydroxypropyl-β-cyclodextrin.

Examples of sugar substitutes include aspartame, saccharin and sodium cyclamate.

Examples of taste modifying agents include cocoa powder, mint in vegetable form, aromatic powder, mint in the form of oil, borneol and powdered cinnamon.

Examples of surfactants and emulsifiers include in particular polysorbate 20, 60, 80, sucroester (7-11-15), poloxamer 188, 407, PEF 300, 400 and sorbitan stearate.

Examples of solubilising agents include miglyol 810, 812, glycerides and their derivatives and propylene glycol.

Examples of exfoliating agents include, for example, polyvinyl pyrrolidone, sodium carmellose or alginic acid or a salt of the latter such as sodium alginate.

Examples of lubricants include magnesium stearate, stearyl magnesium fumarate, behenic acid and its derivatives.

The pharmaceutical compositions according to this invention may also contain another crystalline form of (−)-modafinil or (+)-modafinil respectively, in particular form I and/or another active ingredient or inactive ingredient as a mixture with one or more other polymorphic forms of modafinil such as form III, form II, form IV and form V.

For the purposes of this invention the term "pharmaceutically acceptable vehicle" covers solvents, dispersion media, antifungal and antibacterial agents, isotonic agents and absorption-delaying agents. The use of such media and agents for pharmaceutically active substances is well known to those skilled in the art.

The invention also relates to the use of the forms CRL 40982 form II, CRL 40982 form III, CRL 40982 form IV or CRL 40982 form V of (−)-modafinil and the forms CRL 40983 form II, CRL 40983 form III, CRL 40983 form IV or CRL 40983 form V of (+)-modafinil respectively for the manufacture of a medication intended for the prevention and/or treatment of a condition selected from hypersomnia, in particular idiopathic hypersomnia and hypersomnia in patients affected by a cancer treated by morphine analgesics to relieve pain; sleep apnoeas, excessive somnolence associated with a disease, obstructive sleep apnoeas, narcolepsy; somnolence, excessive somnolence, excessive somnolence associated with narcolepsy; disturbances of the central nervous system such as Parkinson's disease; protection of the cerebral tissue against ischaemia, alertness disturbances, in particular alertness disturbances associated with Steinert's disease, attention disturbances, for example associated with hyperactivity (ADHD); the condition of fatigue, in particular that associated with multiple sclerosis and other degenerative diseases; depression, the depressive condition associated with low exposure to sunlight, schizophrenia, rotating shift working, time shifts; eating disturbances, in which modafinil acts as an appetite stimulant, the stimulation of cognitive functions in low doses.

Process for the Preparation Optically Active Modafinil

In accordance with another aspect the invention relates to a process for preparation of the optical enantiomers of modafinil from (±) modafinil acid, the said process comprising the following stages:
   i) separating the two optical enantiomers of (±) modafinil acid and recovering at least one of the enantiomers,
   ii) placing one of the two enantiomers obtained in contact with a lower alkyl haloformate and an alcohol in the presence of a base,
   iii) recovering the product obtained,
   iv) converting the ester obtained in stage iii) into an amide,
   v) recovering the product obtained in stage iv).

Preferably the lower alkyl haloformate is a lower alkyl chloroformate and, better still, it comprises methyl chloroformate.

Advantageously the lower alkyl haloformates, among which in particular methyl chloroformate, used in this process to bring about the esterification of modafinil acid are less toxic than the dimethyl sulphate described in the process in the prior art U.S. Pat. No. 4,927,855, giving equivalent or better yields. The process is therefore easier to use and more suitable for industrial application.

Preferably the operation is conducted in the presence of an equimolar quantity of lower alkyl haloformate and base in stage ii) in relation to optically active modafinil acid.

It is particularly preferred to use organic bases, more preferably nitrogen-containing bases.

As a particularly preferred base mention may be made in particular of triethylamine, diisopropylamine, diethylmethylamine, diisopropylethyl amine, 1,8-diazabicyclo[5.4.0]undec-7-ene (DBU).

Preferably the solvent used in stage ii) is a lower aliphatic alcohol such as methanol, ethanol or propanol, methanol being particularly preferred.

According to a particular embodiment the ester obtained from stage ii) is crystallised by the addition of iced water.

Conversion of the ester to amide in stage iv) preferably consists of ammonolysis, i.e. treatment with ammonia.

In this context it is generally preferably to work with an excess of ammonia.

According to a particularly advantageous variant of the invention, ammonia is used in the form of gas.

In a preferred embodiment the ammonolysis reaction is performed in a polar solvent, preferably a protic solvent such as lower aliphatic alcohols, for example in methanol or ethanol, methanol being particularly preferred.

The (+) or (−)modafinil acid ester in stage iii) and the (+) or (−)modafinil respectively in stage iv) are recovered using conventional methods known to those skilled in the art.

According to another aspect the invention relates to a process for the preparation of optical enantiomers of modafinil comprising the following stages:
   a. resolving the two optical enantiomers of (±) modafinil acid or salts of the same according to a preferential crystallisation process,
   b. converting the said isolated enantiomers into an amide,
   c. recovering the modafinil enantiomer obtained.

According to a preferred embodiment stage b) is performed in two stages:
   b1) converting the said enantiomers into a lower alkyl ester,
   b2) converting the product obtained in stage b1) into an amide.

According to a particularly preferred embodiment stage b1) is carried out in the presence of a lower alkyl haloformate, an alcohol and a base, under the conditions described previously.

According to a particularly advantageous embodiment, when b1) is performed in the presence of methyl chloroformate, a base and an alcohol and c1) comprises an ammonolysis such as described previously, this process in which the (±)-modafinil acid is separated by preferential crystallisation gives rise to an overall yield generally of the order of 25%. Thus the yield of the (−)-modafinil enantiomer in particular obtained by this process is markedly greater than that is obtained in U.S. Pat. No. 4,927,855.

The preferential crystallisation technique is a technique which is widely used in laboratories and in industry.

This method is based on the alternate crystallisation of two chiral compounds referred to as R and S, forming a conglomerate in solvent A and over a given temperature range $D_T$. This means that within this temperature range any mixture of the two antipodes in thermodynamic equilibrium with the solution comprises two types of crystals each of which only contain molecules having the same configuration, which may or may not incorporate solvent molecules (solvates). The existence of such a conglomerate, without miscibility in the solid state, is implicitly accepted in what follows, at least during the temperature range $D_T$ and in the case of solvent A.

Two kinds of factors influence crystallisation of the optical antipodes, on the one hand parameters associated with ternary heterogeneous equilibria and on the other hand factors affecting the kinetics of crystallisation.

The parameters associated with ternary heterogeneous equilibria comprise:
  the positions of the crystallisation surfaces for the solid species which are deposited at each temperature and more particularly the solubilities of the stable and metastable phases, of the s(+) racemic mixture and the antipodes s(+)=s(−) in relation to temperature, and the ratio of solubilities $\alpha = s(\pm)/s(+)$,
  the extent of the stable and metastable domains for the solid solutions, the racemate, the racemic solvate, the active solvates and the polymorphic varieties of the crystallised solids.

The factors acting on the kinetics of crystallisation include:
  factors internal to the crystals, associated with the bonds between molecules, which cannot be modified by the experimenter,
  external factors which can be modified by the experimenter; these are the nature of the solvent, the nature and concentration of impurities, the supersaturation acquired in relation to time, the temperature range $D_T$, the speed and manner of stirring, the mass and particle size of the nuclei, the wall effect, etc.

These two kinds of factors directly influence the yield, the purity of the phases obtained and the conduct of the separation operations. The feasibility of filtration also depends on the particle size spectrum and the habits of the crystals, the viscosity of the suspension, the vapour pressure of the solvent, the supersaturation of each of the antipodes and the possible presence of a true racemate of a metastable nature. These choices may also affect the kinetics of racemisation of the antipodes or degradation of the molecule.

For each combination comprising the pair of antipodes (R and S) and the solvent (A), the factors affecting the kinetics are of a particular type.

Two preferred methods of crystallisation are mainly distinguished:
  conventional processes, described as SIPC, for "Seeded Isothermal Preferential Crystallization" and their polythermic variants, and
  the process referred to as AS3PC, for "Auto-Seeded Polythermic Programmed Preferential Crystallization".

In the AS3PC preferential crystallisation method which is referred to as being auto-seeded, the system is placed under conditions such that it itself generates its own seeds to produce the required enantiomer, while in the SIPC method these seeds are introduced by seeding. The two types of processes are described in greater detail below.

For more information concerning resolution processes by preferential crystallisation by the AS3PC methods reference may be made in particular to the documents by G. Coquerel, M.-N. Petit and R. Bouaziz, Patent EP 0720595 B1, 1996, E. Ndzié, P. Cardinaël, A.-R. Schoofs and G. Coquerel, *Tetrahedron Asymmetry*, 1997, 8(17), 2913-2920, L. Courvoisier, E. Ndzie, M.-N. Petit, U. Hedtmann, U. Sprengard and G. Coquerel, Chemistry Letters, 2001, 4, 364-365.

According to a particular embodiment, the process for resolution of the optical enantiomers of (±) modafinil acid or its salts is a seeded SIPC or S3PC process, the said process comprising the following stages:
  a) homogenisation of an combination comprising a racemic mixture of crystals in the form of a conglomerate of the first enantiomer of modafinil acid at a temperature $T_D$, for which the defining point E, defined by the variables concentration and temperature $T_D$, lies within the monophase domain of the dilute solution,
  b) rapidly cooling the solution prepared in stage a) initially at the temperature $T_D$ down to the temperature $T_F$,
  c) seeding the solution obtained in stage b) while cooling (i.e. between $T_L$ and $T_F$) or when cooling is complete (i.e. at $T_F$) with very pure seeds of the first enantiomer,
  d) harvesting crystals of the first enantiomer,
  e) adding the racemic mixture of crystals in the form of conglomerate to the mother liquors resulting from the harvest performed in stage d) and homogenising the new combination by heating to a temperature $T_D$, so that the defining point E' is symmetrical for E with respect to the plane of the racemic mixture of the solvent, antipode (−), antipode (+) system, the said point E' lying within the monophase domain of the dilute solution,
  f) rapidly cooling the solution obtained in stage e), initially at temperature $T_D$, down to temperature $T_F$,
  g) seeding the solution obtained in stage f) with very pure seeds of the second enantiomer,
  h) harvesting the crystals of the second enantiomer,
  i) adding the racemic mixture in the form of a conglomerate of crystals resulting from the crystal harvest made in stage h) to the mother liquors and homogenising the new combination by heating to a temperature $T_D$ in order to obtain a composition identical to that of the combination having the initial defining point E,
  j) repeating stages a), b), c), d), e), f), h) and j) to subsequently obtain the first and then the second of the two enantiomers.

Reference is frequently made to these two methods by describing them as "SIPC" and "S3PC" respectively, the latter being a variant of SIPC as described in detail further on in the description.

In what follows, for the purposes of this invention,
  $T_F$ represents the temperature at the end of crystallisation and filtration, located in the three-phase domain,
  $T_L$ represents the homogenisation temperature of the racemic mixture,
  $T_D$ represents the starting temperature at which the starting mixture is a homogenous solution,
  antipode means an enantiomer.

Preferably the process for the resolution of these two optical enantiomers of (±)-modafinil acid or salts of these by preferential crystallisation is an AS3PC self-seeded process, the said process comprising the following stages:

a) creating a combination comprising a racemic mixture of the crystals in the form of a conglomerate of the first enantiomer of modafinil acid and solvent, for which the defining point E, defined by the variables concentration and temperature $T_B$, lie within the two-phase domain of the enantiomer in excess, and is in equilibrium with the saturated solution, b) applying a temperature cooling programming function to the two-phase mixture prepared in stage a), this programming function being such that the mother liquors remain slightly supersaturated, encouraging growth of the enantiomer present in the form of crystals while preventing spontaneous nucleation of the second enantiomer present in the solution, c) throughout the time of crystal growth in stage b) adopting a rate of stirring which increases slightly in relation to time so that it is at all times sufficiently slow to encourage growth of the first enantiomer while avoiding the generation of excessively large shear forces bringing about uncontrolled nucleation but sufficiently fast to achieve a homogeneous suspension and rapid renewal of the mother liquor around each crystallite of the first enantiomer, d) harvesting the crystals of the first enantiomer, e) adding the racemic mixture of crystals in the form of a conglomerate to the mother liquors resulting from the harvest performed in stage d) and bringing the new combination to a temperature threshold $T_B$ during the time necessary to achieve thermodynamic equilibrium so that the defining point E' is symmetrical for E with respect to the plane of the racemic mixtures for the solvent, antipode (−), antipode (+) system, the said point E' lying within the two-phase domain of the second enantiomer which is in excess and in equilibrium with its saturated solution, f) applying the same cooling programming function as in stage b) to the two-phase mixture prepared in stage e) containing the second enantiomer so that the mother liquors remain slightly supersaturated during crystallisation in order to encourage growth of the enantiomer present in the form of crystals while preventing spontaneous nucleation of the first enantiomer present in the solution, g) adopting a stirring speed which increases slightly in relation to time over the entire time of crystal growth in stage f) so that it is at all times sufficiently slow to encourage growth of the second enantiomer while avoiding generation of excessively large shear forces giving rise to uncontrolled nucleation, but sufficiently fast to obtain a homogeneous suspension and rapid renewal of the mother liquor around each crystallite of the second enantiomer, h) harvesting crystals of the second enantiomer, i) adding the racemic mixture of crystals in the form of conglomerate to the mother liquors resulting from the crystal harvest performed in stage g) in order to obtain a combination in which the composition is identical to that of the initial combination E, j) repeating stages a), b), c), d), e), f) g), h) and i) to obtain the first and then the second of the two enantiomers successively.

In what follows, for the purposes of this invention, $T_{HOMO}$ shall mean the homogenisation temperature of the combination comprising the racemic mixture, the first enantiomer and the solvent.

Thus in stage (a) of the process according to the invention the choice of the solvent or solvents and the working temperature range are defined in such a way so as to obtain simultaneously:

antipodes which form a conglomerate and of which any racemate is metastable in the working temperature range, liquors which are sufficiently concentrated but of low viscosity and low vapour pressure, the absence of solvolysis and racemisation, stability of the solvates if these are present at equilibrium and they are resolvable enantiomers.

In stages (a) and (e) of the process according to the invention, the temperature $T_B$ is higher than the temperature $T_L$ for homogenisation of the quantity of racemic mixture present in the initial suspension, in that from the curve for the change in $T_{HOMO}$ in relation to the excess of enantiomer and for a constant concentration of the racemic mixture $X_L$ the said temperature $T_B$ is defined in such a way that the mass of fine crystals of the first enantiomer from stages (a) and (i) and the second enantiomer from stage (e), in equilibrium with their saturated solutions, represent at most 50% and preferably between 25% and 40% of the expected harvest.

In stages (b) and (f) of the process according to the invention, the function for programming cooling from temperature $T_B$ to $T_F$, appropriate to the experimental assembly, is defined so as to:

achieve slight supersaturation throughout the time for crystallisation of the enantiomer present in the form of crystals at the start of each cycle, this slight supersaturation giving rise to gentle growth and secondary nucleation, achieve maximum supersaturation of the other enantiomer at $T_F$ without primary nucleation, obtain a harvest of crystals in stages (d) and (h) which after addition of the racemic mixture and the provision of make-up in stages (e) and (i), makes it possible to perform the operations cyclically.

In fact every experimental assembly has an influence on the supersaturation capacities of the mixtures used and the efficiency of stirring, and as a consequence the function programming cooling must be adapted to the circumstances in which the process is carried out. However the temperature $T_B$, the solubilities of the racemic mixture in relation to temperature, and the $T_{HOMO}$ curve in relation to the excess of enantiomer for a constant concentration of the racemic mixture $X_L$ are themselves wholly independent of the experimental assembly.

The cooling programming function, which is the function linking temperature with time, is determined in its part from $T_L$ to $T_F$ by cooling of the solution of concentration $X_L$ from $T_L+1°$ C. to $T_F$, where $T_F$ is lower than $T_L-(T_{HOMO}-T_L)$, in order to obtain a stable saturated solution without primary nucleation while permitting a double harvest of the initial enantiomer excess and the said cooling programming function is determined in its part from $T_B$ to $T_L$ by extrapolation of the same function as established from $T_L+1°$ C. to $T_F$.

The process for the preferential crystallisation of (±)-modafinil acid or salts of the same has other advantageous features alone or in combination such that:

in stages (a) and (i) the mass of fine crystals of the first enantiomer in equilibrium with the saturated solution represents between approximately 25% and 40% of the expected harvest, 50% representing a maximum limit, in stage e) the mass of fine crystals of the second enantiomer in equilibrium with its saturated solution represents between approximately 25% and 40% of the expected harvest, 50% representing a maximum limit, in stages (b) and (f) the heat released accompanying deposition of the first enantiomer and the second enantiomer is incorporated into the temperature programming function, in stages (e) and (i) compensatory additions of solvent are made, in stages (a), (e) and (i) the fine crystals of the racemic mixture in the form of conglomerate added were subjected to prior treatment to accelerate the dissolution stage, such as grinding and sieving, treatment with ultrasound waves or partial lyophilisation, before being added; these treatments being also for the purpose of providing fine crystals capable of generating a large surface area for crystal growth, in stages (a), (e) and (i) involving dissolution, the rate of stirring is high in comparison with stages (c) and (g).

In addition to the heterogeneous equilibrium data required for implementing the AS3PC process, the operations are also subject to adjustable kinetic constraints, particularly the cooling function, and these are specific to each solvent/enantiomer combination.

According to one embodiment the solvent used in stage a) of the SIPC, S3PC or AS3PC processes is absolute or denatured ethanol, possibly in a mixture with an organic or mineral base, or with one or more solvents capable of improving the solubility of the racemic mixture in ethanol.

As a variant, the solvent used in stage a) of the SIPC, S3PC or AS3PC processes is 2-methoxyethanol or methanol, possibly mixed with an organic or mineral base, and/or one or more solvents capable of improving the solubility of the racemic mixture in ethanol.

According to a particularly advantageous embodiment the solvent used in stage a) of the SIPC or AS3PC process is ethanol, 2-methoxyethanol or methanol. For (±)-modafinil acid the filtration temperature $T_F$ preferably lies between 0° C. and 40° C.

In the case of ethanol the temperature $T_F$ preferably lies between 0° C. and 25° C., and better still it is close to 18° C. or 17° C.

In the case of 2-methoxyethanol or methanol, the temperature $T_F$ preferably lies between 20° C. and 35° C. and in particular is close to 30° C.

Preferably the concentration of the racemic mixture in stage a) then lies between 2 and 50% by mass, more preferably between 2 and 30% by mass, and, better still, close to 5.96% by mass in the case of ethanol, 15.99% in the case of 2-methoxyethanol and 25.70% in the case of methanol.

In this context it is most particularly preferred that the enantiomer excess in stage a) should be between 1 and 50% by mass, more preferably between 1 and 20% by mass, and, better still, close to 11% by mass in the case of ethanol, 8% by mass in the case of 2-methoxyethanol and 10% by mass in the case of methanol.

In the SIPC and S3PC processes the temperature $T_D$, the temperature at which the starting mixture is a homogeneous solution, depends on concentration and then generally lies between 35° and 50° C. when the solvent is under reflux. The cooling from temperature $T_D$ to $T_F$ is very fast so as to remain within the monophase domain and is preferably carried out in less than 20 min, for example by quenching.

According to a preferred embodiment of the AS3PC process the temperature $T_B$ then lies between the temperatures $T_L$ and $T_{HOMO}$. The temperature $T_B$ may in particular lie between 25° C. and 50° C.

By way of example, in the case of ethanol, when the enantiomer excess is close to 11% by mass temperature $T_B$ preferably lies between 25° C. and 40° C., in particular between 30.1° C. and 36.2° C. and more preferably close to 33.5° C. or 31.5° C.

In the case of 2-methoxyethanol, when the enantiomer excess is close to 8% by mass temperature $T_B$ preferably lies between 35° C. and 50° C., in particular between 39.1° C. and 47.9° C. and more preferably close to 41° C.

In the case of methanol, when the enantiomer excess is close to 10% by mass, temperature $T_B$ preferably lies between 40° C. and 55° C., in particular between 45.1° C. and 53.9° C. and more preferably close to 46.5° C.

It is most particularly preferred that cooling from $T_B$ to $T_F$ in stage b) be carried out in a time which is sufficiently long for the average mass of desired enantiomer crystals harvested to be large, but sufficiently short to prevent the other enantiomer from crystallising, thus obtaining a high optical purity, in particular greater than 85%. Cooling is generally monitored by polarimetry to determine the right moment for filtration. Preferably cooling takes place between 50 and 70 minutes, better still, it takes 60 minutes when the solvent used is ethanol.

Likewise, the length of the plateau at temperature $T_F$ for the SIPC, AS3PC and S3PC processes is preferably sufficiently great to allow a large mass of the desired enantiomer crystals to be harvested, but not too long so as to prevent the other enantiomer from crystallising at the same time as the desired enantiomer, thus obtaining a high optical purity.

According to a preferred embodiment the length of the temperature plateau $T_F$ lies between 15 and 60 minutes, preferably about 60 minutes.

A person skilled in the art will be able to adjust the rate of stirring to the type of reactor used in SIPC, S3PC or AS3PC processes. By way of indication, for a 2 or 10 liter reactor the speed at which the medium is stirred may be held between 150 and 250 rpm.

In a particularly useful manner these methods of preferential crystallisation make it possible to isolate the optical enantiomers of modafinil, in particular the laevorotatory enantiomer, in yields which are very much greater than those obtained by resolution using a chiral agent. The yields obtained are generally of the order of 90%, or even higher, in relation to the (+) or (−) optical enantiomer, or of the order of 45% or more in relation to the racemic mixture.

AS3PC, SIPC and S3PC Methods

The AS3PC and SIPC methods mentioned above are described below.

Ternary Heterogeneous Equilibria: R and S Antipodes, and Solvent A

For example the work by J. E. Ricci (Ed. Dover Publication Inc. New York, 1966, The Phase Rule and Heterogeneous Equilibrium) deals with the general case of heterogeneous equilibria in ternary systems. The description below will be restricted to particular aspects of the ternary system, A (achiral solvent), R and S (enantiomers which cannot be racemised in the temperature domain used), which are necessary for an understanding of the various processes of preferential crystallisation.

In order to show the special role of the solvent this ternary system will be represented by a right prism having a cross-section which is a right-angled isosceles triangle on which the temperature is plotted on an axis perpendicular to the plane of concentration.

The fact that the thermodynamic variables for the two enantiomers, Tf, ΔHf, solubility in a achiral solvent, etc., are identical has the result that representation of the domains is symmetrical with respect to the vertical plane A-TS-T, which includes the optically inactive mixtures, in FIG. 1. The following simplifications have been made in order to assist an initial description of this system:
- the only phases which crystallise out are the pure constituents in a given arrangement (absence of racemate, solvate and polymorphism in the case of the antipodes),
- miscibility between the independent constituents is zero in the solid state,
- the solvent has a melting point which is appreciably lower than that of the antipodes,
- in the temperature range used the solubility of an antipode is not influenced by the presence of the other in the solution (Meyerhoffer's law is respected), which is reflected in the ratio having the value α=2).

Representation of Ternary Equilibria as a Function of Temperature

FIG. 1 shows the domains for the following phases:
- the monophase domain for the dilute solution (Φ=1),
- the two crystallisation surfaces for the constituents bounding the two-phase domains (Φ=2).
- the surface for deposition of the solvent is confined to the vicinity of A because the melting point of this constituent is appreciably lower than that of the other constituents, in accordance with the conditions mentioned above.
- the three monovariant curves (Φ=3) or eutectic valleys originating from binary eutectic points,
- the ternary eutectic invariant at Tε (Φ=4), above which the three constituents are crystallised.

FIG. 2 shows in a superimposed fashion the two isothermal cross-sections of the ternary displayed in FIG. 1 at $T_D$ and $T_F$. At each temperature the cross-section consists of four domains as detailed in the table below.

| Temperature | Domain boundary | Nature of the phases in equilibrium | Number of phases in equilibrium |
|---|---|---|---|
| $T_D$ | $A$-$S_D$-$I_D$-$S'_D$ | dilute solution | 1 |
| $T_D$ | $R$-$S_D$-$I_D$ | solution + crystals of R | 2 |
| $T_D$ | $S$-$S'_D$-$I_D$ | solution + crystals of S | 2 |
| $T_D$ | $I_D$-$R$-$S$ | solution + crystals of R and S | 3 |
| $T_F$ | $A$-$S_F$-$I_F$-$S'_F$ | dilute solution | 1 |
| $T_F$ | $R$-$S_F$-$I_F$ | solution + crystals of R | 2 |
| $T_F$ | $S$-$S'_F$-$I_F$ | solution + crystals of S | 2 |
| $T_F$ | $I_F$-$R$-$S$ | solution + crystals of R and S | 3 |

Isopleth Cross-Section RYT

FIG. 3 shows the isopleth cross-section R-Y-T which is fundamental to an understanding of crystallisation by the cooling of ternary solutions in thermodynamic quasi-equilibrium. This cross-section is also necessary for following non-equilibrium processes, SIPC, variants and AS3PC. This plane is the geometric locus of the points fulfilling the relationship:

$$X_A/X_S = (1-Y)/Y = \text{constant, with } X_A \text{ and } X_S \text{ providing the fractions by mass of solvent and antipodes } S.$$

In FIG. 3 it is possible to see:
- the monophase domain of the ternary solution,
- the liquidus for antipode R, this curve representing the intersection of plane R-Y in FIG. 2 with the crystallisation surface for that constituent. This stable equilibrium curve originates at the melting point of antipode R (not shown) and is bounded on the low temperature side by point L which forms part of the ternary eutectic valley for the racemic mixtures. This latter curve and the line of the conoid at $T_L$ (horizontal segment at $T_L$) are the boundary of the two-phase domain—saturated solution plus crystals of R. It extends into the underlying three-phase domain through a solubility curve for the same antipode R which is of a metastable nature (dashed lines),
- the three-phase domain: crystals of T and S, plus saturated solution. This domain is bounded at the top by the horizontal line of the conoid for R, and at the bottom by the line of the invariant ternary eutectic plane and on the left by the line Lm of one of the conoids relating to the antipode S.
- the line KL of the crystallisation surface for antipode S which bounds the two-phase domain at the top-saturated solution plus crystals of S. This domain is bounded in its lower part by the lines of the two conoids for S: gm and Lm. The location of the second line Lm of the conoid for S in relation to the metastable solubility curve for R, which is an extension of EL, will be discussed below in relation to the relative position of F1 and F in relation to the ratio of solubilities α,
- The ternary invariant at the temperature Tε above which the three crystallised constituents A, R and S lie.

Change on Cooling and with Thermodynamic Quasi-Equilibrium of the Ternary Solutions Having a Slight Excess of Enantiomer It is taken in what follows that the overall point for the system (i.e. the point representing the overall composition of the mixture) lies on the vertical passing through point E in FIGS. 2 and 3, and its precise position is defined by its temperature (or level). Only the following temperature range is considered:
- $T_D$: temperature at which the starting mixture is a homogeneous solution, and
- $T_F$: temperature at the end of crystallisation and filtration, which lies in the three phase domain.

This overall composition E corresponds to a racemic solution which is slightly enriched by a mass M of the antipode R forming a total mass Mt (the enantiomer excess R−S/R+S generally lies between 4% and 9%). Equilibrium conditions are obtained by very slow cooling and by seeding in the solid phase(s) when the overall point E defining the mixture reaches a domain where this (these) phase(s) is (are) present at equilibrium.

At the starting temperature $T_D$ the solution is homogeneous. The following are observed in succession on cooling:
- crystallisation of the antipode R alone, from $T_{HOMO}$ to $T_L$, at the same time the solution point moves on the solubility curve for antipode R, that is from point E at level $T_{HOMO}$ to point L within the isopleth cross-section R-Y. At point L, mass M of crystals R in equilibrium with saturated solution is given by Mt $(X_E-X_L/1-X_L)$=M and corresponds to the enantiomer excess present in the initial solution (FIG. 3), the abscissas of the points L, E and R correspond to the compositions, and 1 (FIG. 3).
- from $T_L$ the solution point moves from L to $I_F$ along the line of fixed gradient containing the solutions of racemic composition shown in FIG. 2, thus leaving the isopleth cross-section R-Y in FIG. 3, crystals of R and S are then deposited simultaneously and in equal quantities. Resolution cannot be effected under equilibrium conditions at temperatures below $T_L$.

Change in the Solution when Resolving by Conventional Control in Accordance with the SIPC Process Crystallisation of the First Antipode in Excess The previous solution E is homogenised at temperature $T_D$ (FIGS. 4 and 5). In order to make it supersaturated it is cooled rapidly to temperature $T_F$ without any crystallisation occurring. This solution, which is not in thermodynamic equilibrium, is then seeded with very pure seeds of the antipode R having the same chirality as the antipode in excess. The isothermal crystallisation of antipode R is established and the point representing the solution moves within the cross-section R-Y-T from E to the level $T_F$ with which it is first coterminous to F where filtration is rapidly performed. The mass of antipode R recovered is 2M or again is equal to Mt ($X_E$-$X_F$/1-$X_F$).

Crystallisation of the Second Antipode, Cyclicity of the Operations

The above fundamental operation thus gave rise to a solution F enriched with antipode S. By adding a mass 2M of racemic mixture (equal to that of the antipode recovered) and heating this mixture to temperature $T_D$ a homogeneous solution E' which is symmetrical for E with respect to the vertical plane A-(RS)-T is obtained. The process making it possible to obtain a mass 2M of antipode S will itself also be represented by symmetrical movement of the above in relation to this median plane. The following operations are then performed in sequence:

solution E' which is homogeneous at temperature $T_D$ is first cooled to $T_F$, then, seeded with very pure seeds of antipode S, the growth of this antipode displaces the point representing the solution on the horizontal segment E'F' (at the level $T_F$), when the solution point is the same as F', the solution is filtered and provides a mass 2M of antipode S, after a further addition of a mass 2M of racemic mixture and a further heating to $T_D$ a homogeneous solution is again obtained and its representative point is the same as the initial point E at level $T_D$, the rest of the process is merely a repeat of this cycle of operations.

Variants in the SIPC Process

The literature (Amiard, G., 1956, Bull. Soc. Chim. Fr. 447, Collet, A., Brienne, M. J., Jacques, J., 1980, Chemical reviews 80, 3, 215-30, Noguchi Institute, 1968, patent GB 1 197 809) is based on the above general scheme; the main modifications which have appeared in the literature are classified as follows:

a) Spontaneous Primary Nucleation of the Antipode in Excess

When (±)-threonine is separated (Amiard, G., 1956, Bull. Soc. Chim. Fr. 447), the primary nucleation of the antipode in excess occurs spontaneously within the supersaturated homogeneous solution. This primary nucleation occurs when point E representing the composition of the whole lies within the three-phase domain and the solution is not stirred (Collet, A., Brienne, M. J., Jacques, J., 1980, Chemical Reviews 80, 3, 215-30).

b) Seeding During Cooling (S3PC)

This protocol is the one most frequently found in the literature (Noguchi Institute, 1968, patent GB 1 197 809) when the process differs from SIPC. There are differences between the procedures cited, but nevertheless the following common broad lines can be identified:

cooling of the homogeneous solution from $T_D$ to a temperature below to $T_L$ but above $T_F$, seeding of the supersaturated homogeneous solution located in the three-phase domain with seeds of the same chirality as the antipode in excess, cooling to $T_F$. In some cases the latter stage is controlled by precise temperature programming (Noguchi Institute, 1968, patent GB 1 197 809).

These protocols will be grouped together under the same term "S3PC" for "Seeded polythermic programmed preferential crystallization" although temperature programming is not present or is limited to the second stage of cooling.

Change in the Solution Point in the Case of Resolution by Programmed Control and Self-Seeding in Accordance with the AS3PC Process According to the Invention In order to achieve a better comparison between conventional processes and the AS3PC process the initial point E is chosen arbitrarily in FIGS. 6 and 7 to be the same as in the previous case; however, as will be apparent in the examples which follow, the AS3PC process makes it possible to take a point E which is further away from the plane A-(RS)-T and therefore with a larger enantiomer excess and thus improve the harvest of crystals in each operation.

Crystallisation of the First Antipode in Excess

At the start of the process, and contrary to conventional protocols, the whole, crystals plus solution, is no longer homogeneous but is raised to the temperature $T_B$. The initial solution is then in equilibrium with the crystals of the enantiomers in excess (for example R in FIG. 7). The points representing the solution ($S_E$) and the whole (E) are therefore not the same from the start of the process. The two-phase mixture is subjected to a programmed temperature reduction function without the addition of seed crystals. The point representing the solution describes a curve $S_E$F, contained within the plane R-Y-T, which depends on the kinetics of cooling (FIG. 7). With correctly adjusted kinetics, growth of the enantiomer crystals in excess occurs at the start, crystallisation then progressing towards a simultaneous regimen of growth plus secondary nucleation. When the point representing the solution reaches the point F, filtration is performed to recover a mass 2M of crystals of antipode R.

Crystallisation of the Second Antipode, Cyclic Nature of the Operations

From point F, which corresponds to the above parent solution, there is a move to point E, which is symmetrical for E with respect to the vertical plane A-(RS)-T, by adding a mass 2M of the racemic mixture and heating to temperature $T_B$. The enantiomer excess is then profited from to take up a position in the two-phase domain containing the saturated solution and the crystals of the antipode in excess. To begin with the racemic mixture added during the passage from F to E (as from F' to E) will be ground and sieved so as to accelerate the stage of dissolution of the two antipodes and more particularly the antipode of which there is less, and thus permit the formation of a large number of crystals of the antipode in excess which has the role of the seeds added in conventional processes.

The saturated solution $S'_E$, which is symmetrical for $S_E$ with respect to the plane A-(RS)-T is subjected to the same cooling function. The crystals present from the start of cooling grow and then take part in a double mechanism of growth+secondary nucleation. As in the case of the first crystallisation no seeding is therefore necessary.

During this time the point representing the solution moves along a curve SEE contained within the plane of the isopleth cross-section S—Y'-T which is symmetrical with respect to the bisecting plane A-(RS)-T.

When the solution reaches the representative point located at F', filtration is performed to harvest a mass 2M of ground and sieved racemic mixture followed by raising the temperature to $T_B$ yielding the two-phase mixture at the starting equilibrium.

Continuation of the process consists of repeating this cycle of operations yielding crystals of antipode R and S alternately.

Necessary Conditions for Implementing the AS3PC Process a) The equimolar mixture of optical antipodes produces a conglomerate (pure antipodes or solvates) in the solvent used within the temperature range $T_B$-$T_F$; however the existence of a metastable racemate is not a handicap.

b) The molecules which are to be resolved are stable in this solvent and in the temperature range used between $T_B$ and $T_F$.

c) It is necessary to determine the ternary equilibrium temperatures $T_L$ and $T_{HOMO}$. Temperature $T_L$ is the temperature at which the racemic mixture dissolves in the absence of any enantiomer excess in the solution. Once $T_L$ has been determined, the temperature $T_{HOMO}$ corresponds to the homogenisation temperature of the solution. It depends on the starting enantiomer excess and the ratio α of the solubilities of the racemic mixture and the antipode at $T_L$. Knowledge of the supersaturation capacities of the solutions between $T_L$ and $T_F$ is also necessary, depending upon the cooling kinetic, the form of stirring, the nature of the vessel and the particle size of the crystals of the antipode in excess. To a first approximation, the time to the appearance of crystals by primary nucleation in the homogeneous racemic solution L cooled from a temperature slightly above $T_L$ using the same kinetics yields an indication of the supersaturation capacity tolerated by the conglomerate under these experimental conditions. This method of operation has been taken into account in the examples.

d) Knowledge of the kinetics of dissolution of a known mass of racemic mixture (of a given particle size) dispersed in the solution at temperature $T_B$. A few tests will be sufficient to discover this time.

In what follows the examples and figures are provided by way of a non-restrictive illustration of this invention.

FIGURES

All the isothermal cross-sections and isopleths illustrated in these figures have composition variables expressed as fractions by mass.

Figure 1:
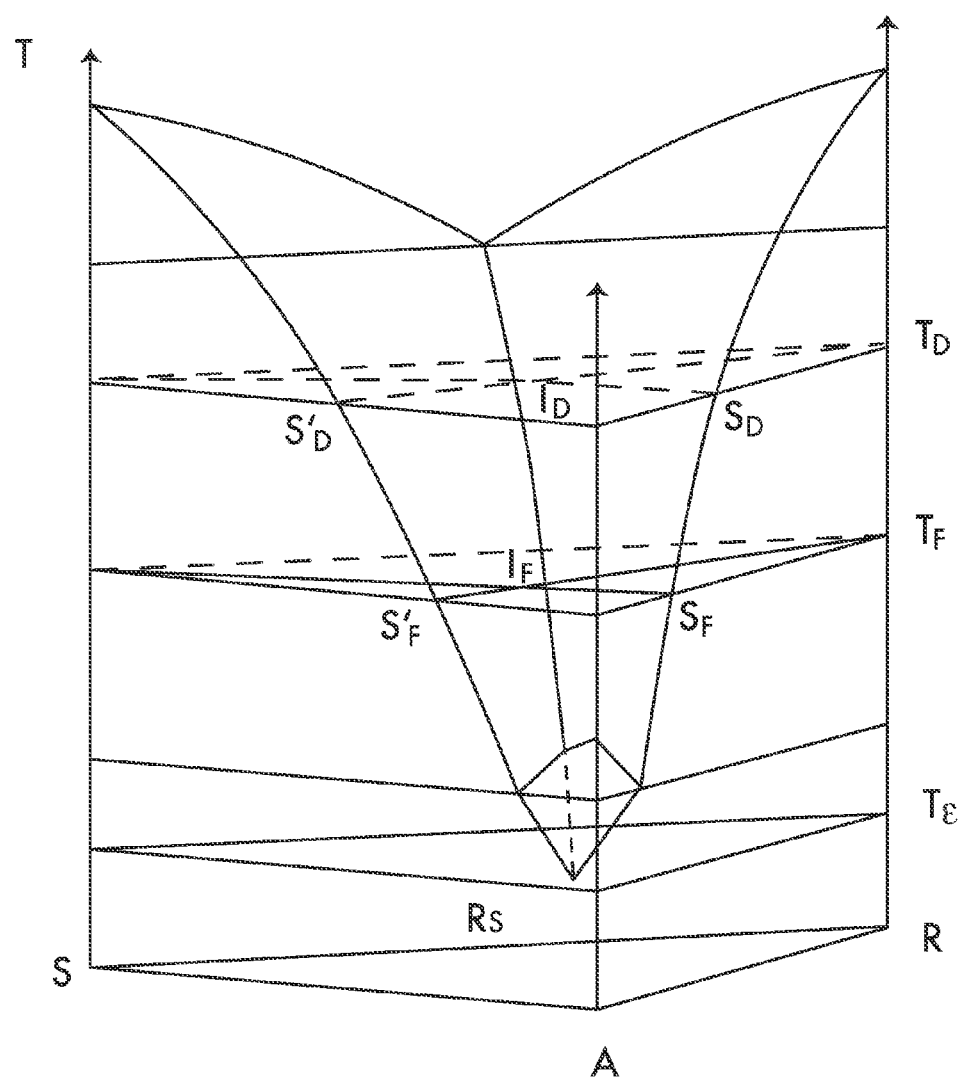
FIG. 1 is a perspective view of the ternary system solvent A-antipode R-antipode S, in relation to temperature and crystallisation surfaces for each constituent and compositions of the doubly saturated solutions (monovariant curves); this figure also shows the isotherms at temperatures $T_D$ and $T_F$ and the ternary eutectic plane at the temperature Tε including four phases.
Figure 2:
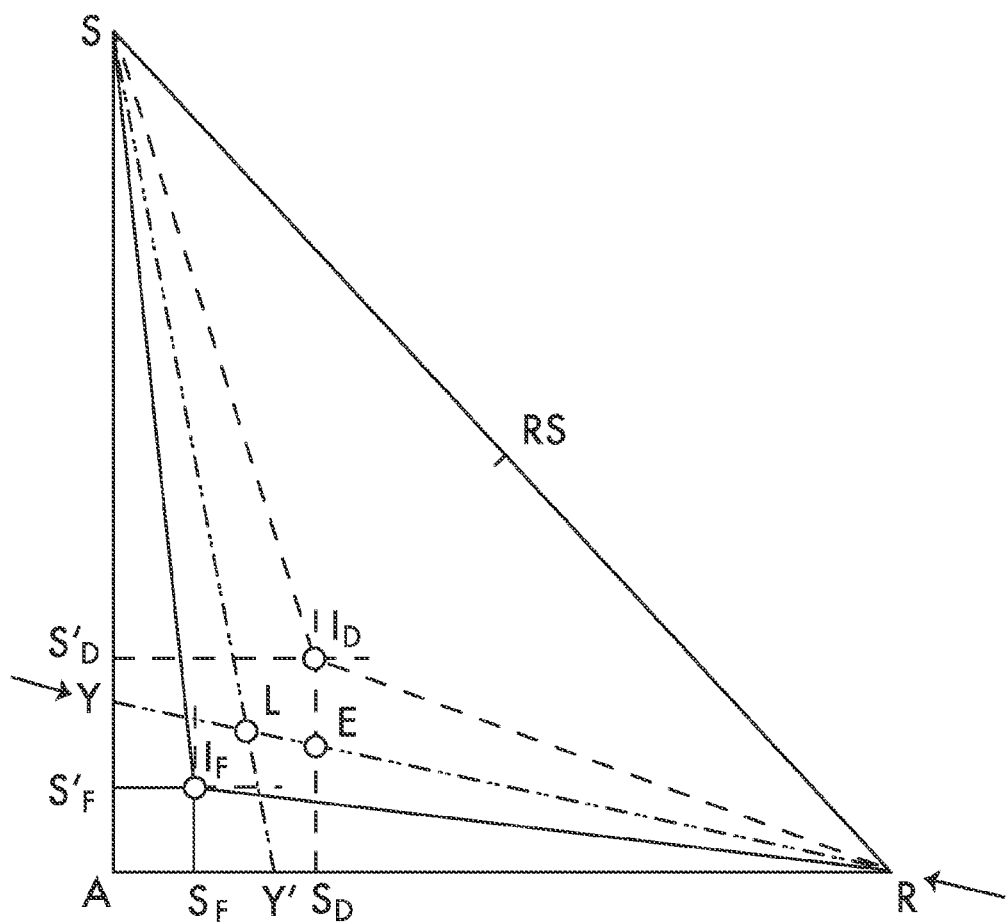
FIG. 2 is a projection onto the plane of concentrations of the equilibria at $T_D$ and $T_F$, as well as a representation of the line of the isopleth cross-section RY on which point E represents the composition of the initial mixture slightly enriched in antipode R which will deposit this same antipode.
Figure 3:
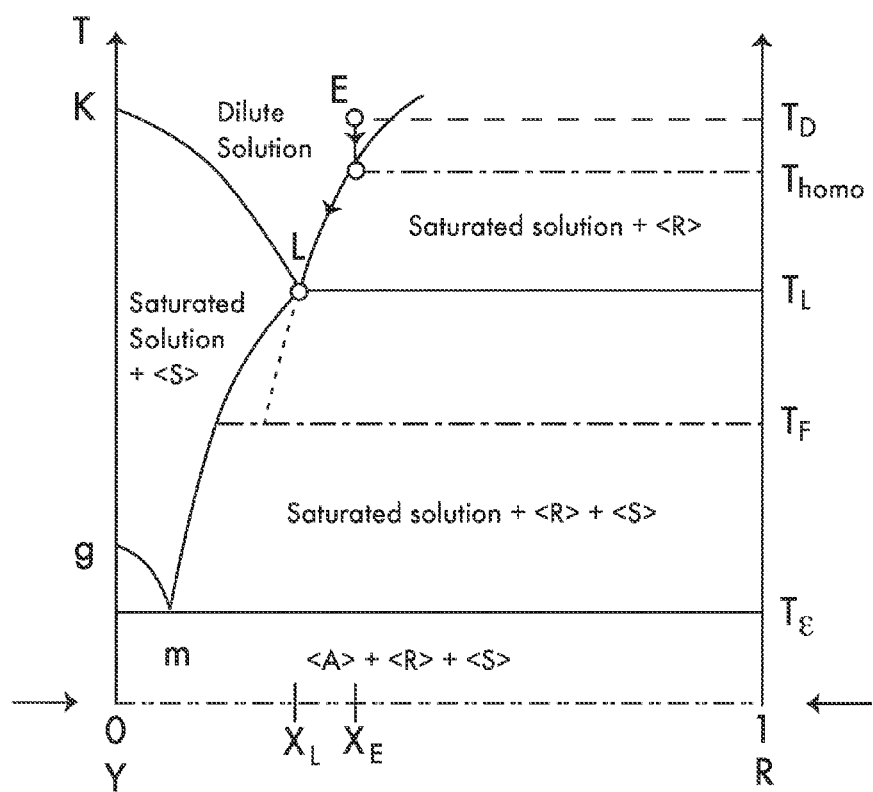
FIG. 3 is the isopleth vertical cross-section RY in FIG. 2 containing the composition points for the antipode in excess and that of the initial solution E on which the path of the solution point for a mixture of composition $X_E$ at equilibrium and on cooling is shown (as a bold line). For T<$T_L$ the solution point no longer falls within this cross-section.
Figure 4:
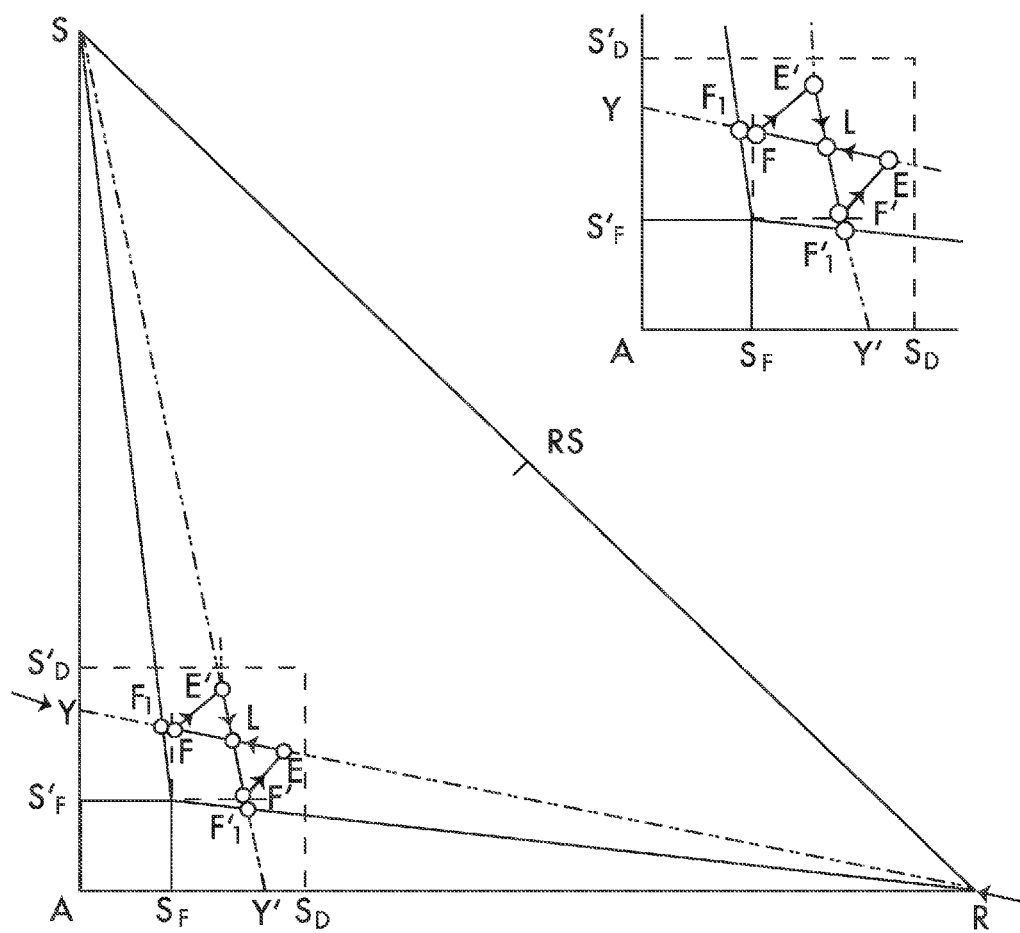
FIG. 4 is a projection onto the concentrations plane of the path of the solution point (as a bold line) during alternating resolution by isothermal control at temperature $T_F$ and seeded in accordance with the SIPC method.
Figure 5:
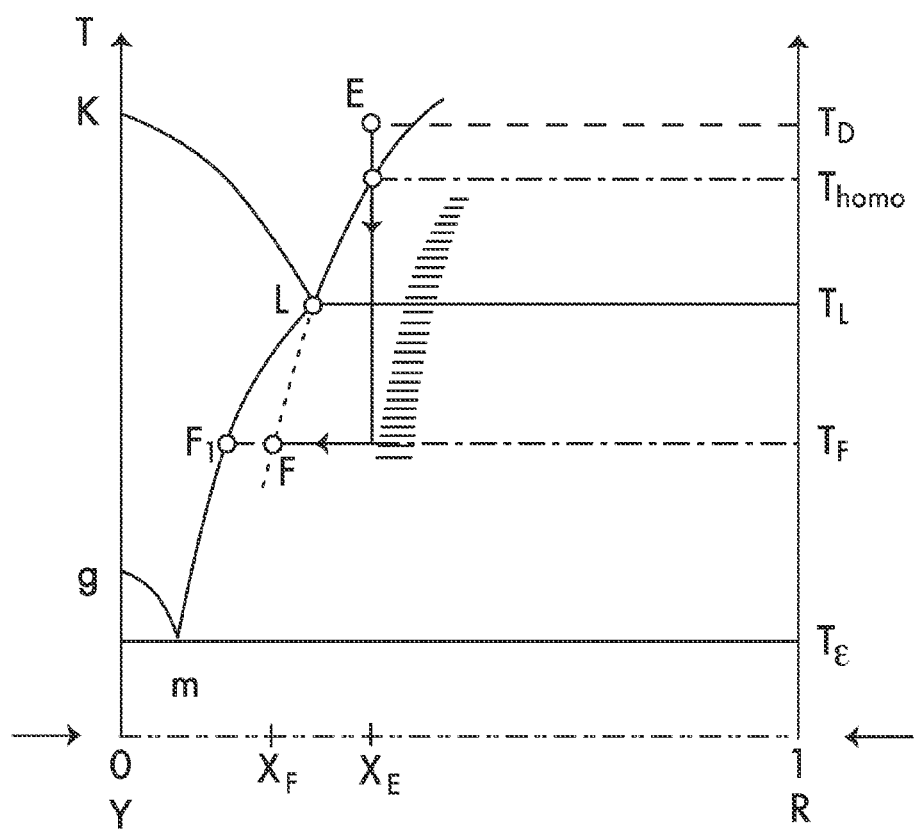
FIG. 5 is the vertical isopleth cross-section containing the straight line RY in FIG. 4 and illustrating the path of the solution point (as a bold line) from E to F during isothermal control (to $T_F$) and seeded according to the SIPC method.
Figure 6:
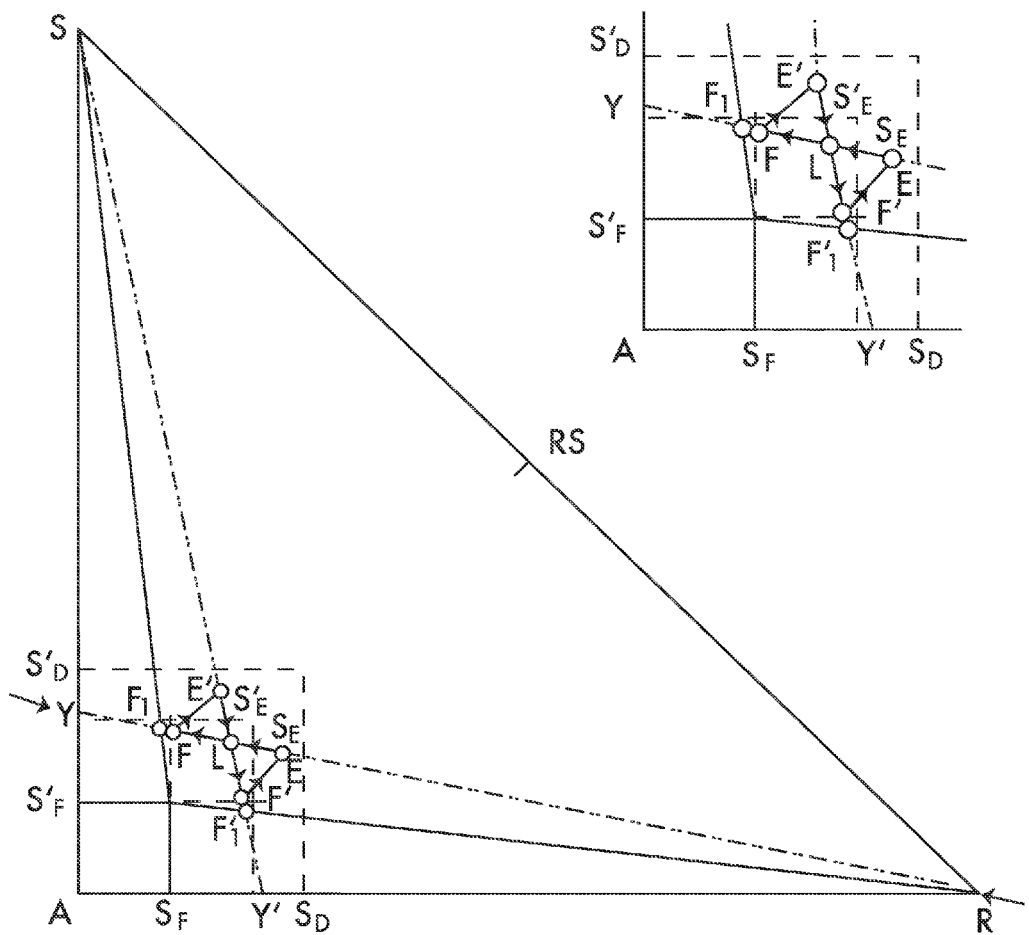
FIG. 6 is a projection onto the concentrations plane of the path of the solution point (as a bold line) when resolving by the self-seeded programmed polythermal process (AS3PC).
Figure 7:
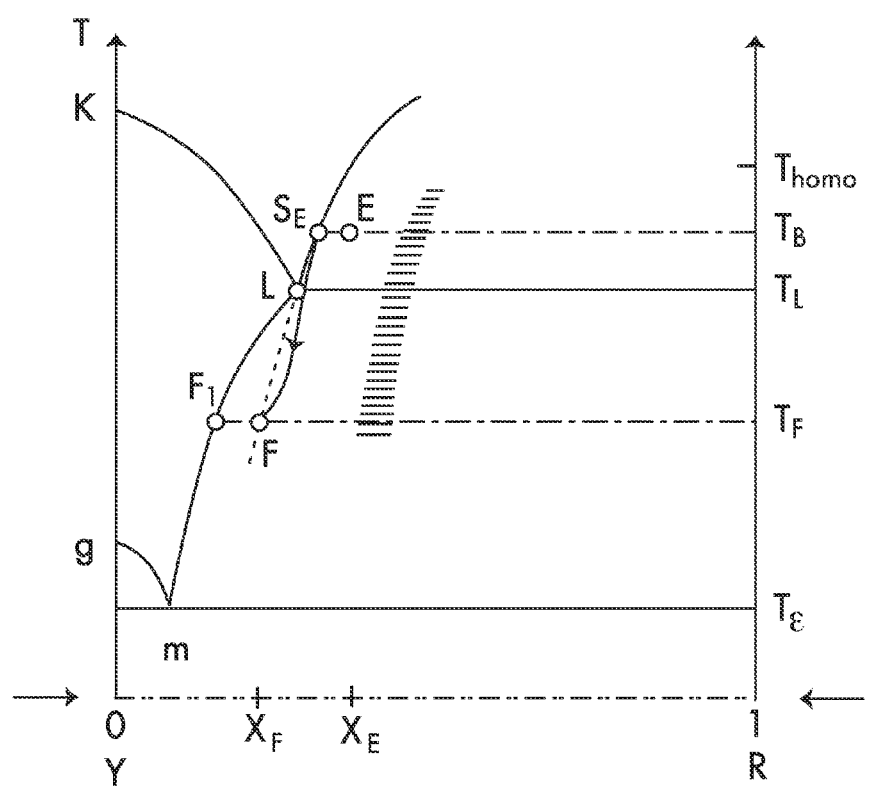
FIG. 7 is the vertical isopleth cross-section containing the straight line RY in FIG. 6 and illustrating the path of the solution point (as a bold line) from $S_E$ to F during resolution by the self-seeded programmed polythermal process according to the invention (AS3PC).
Figure 8:
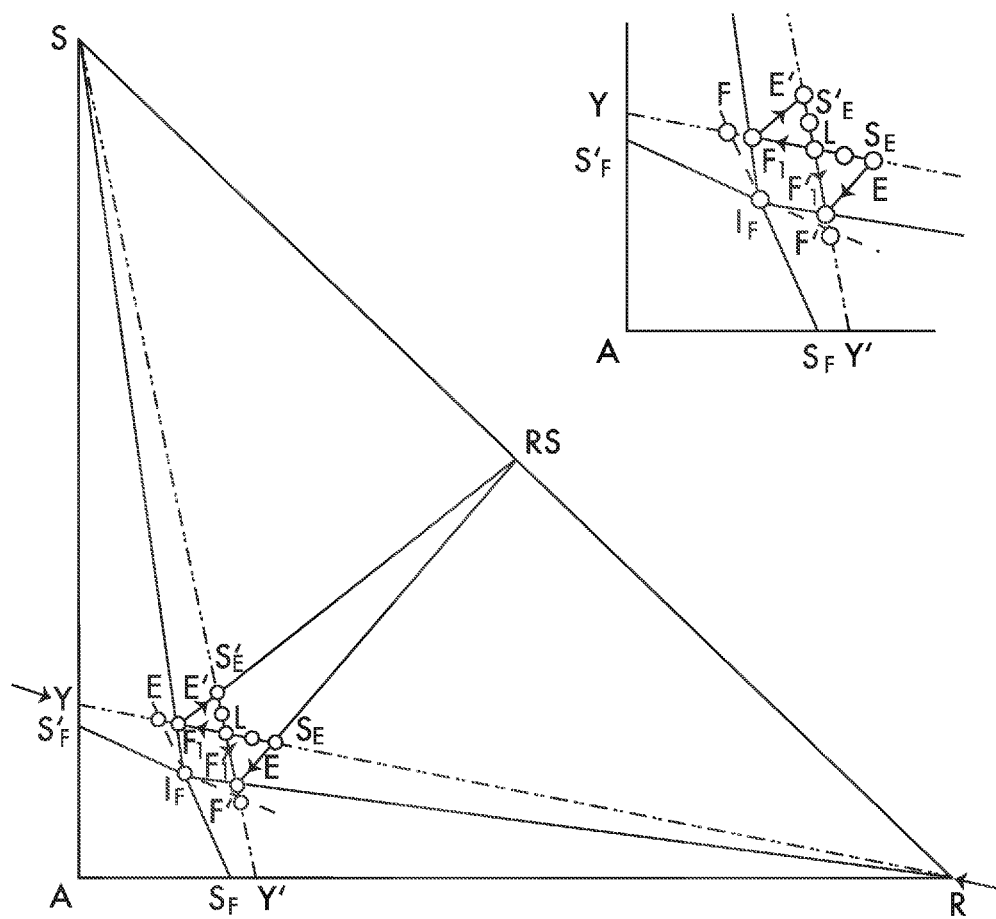
FIG. 8 is a projection on the concentrations plane of the path of the solution point (as a bold line) during resolution by the self-seeded programmed polythermal process (AS3PC) and confirming the relationship s(±)<2−α.
Figure 9:
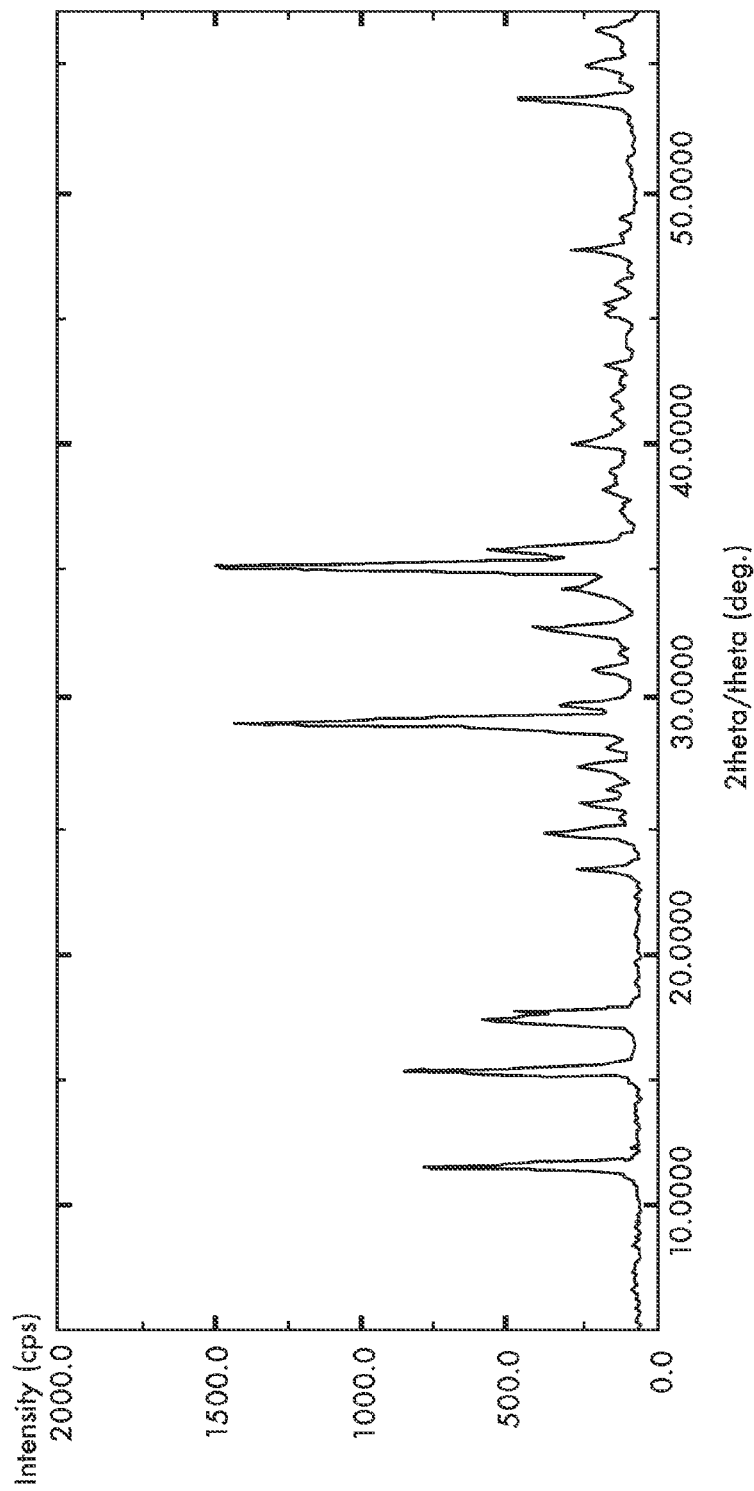

FIG. 9 shows the powder X-ray diffraction spectrum obtained corresponding to form II of the laevorotatory enantiomer and dextrorotatory enantiomer of modafinil respectively (Diffractometer: Miniflex Rigaku (Elexience).

Figure 10:
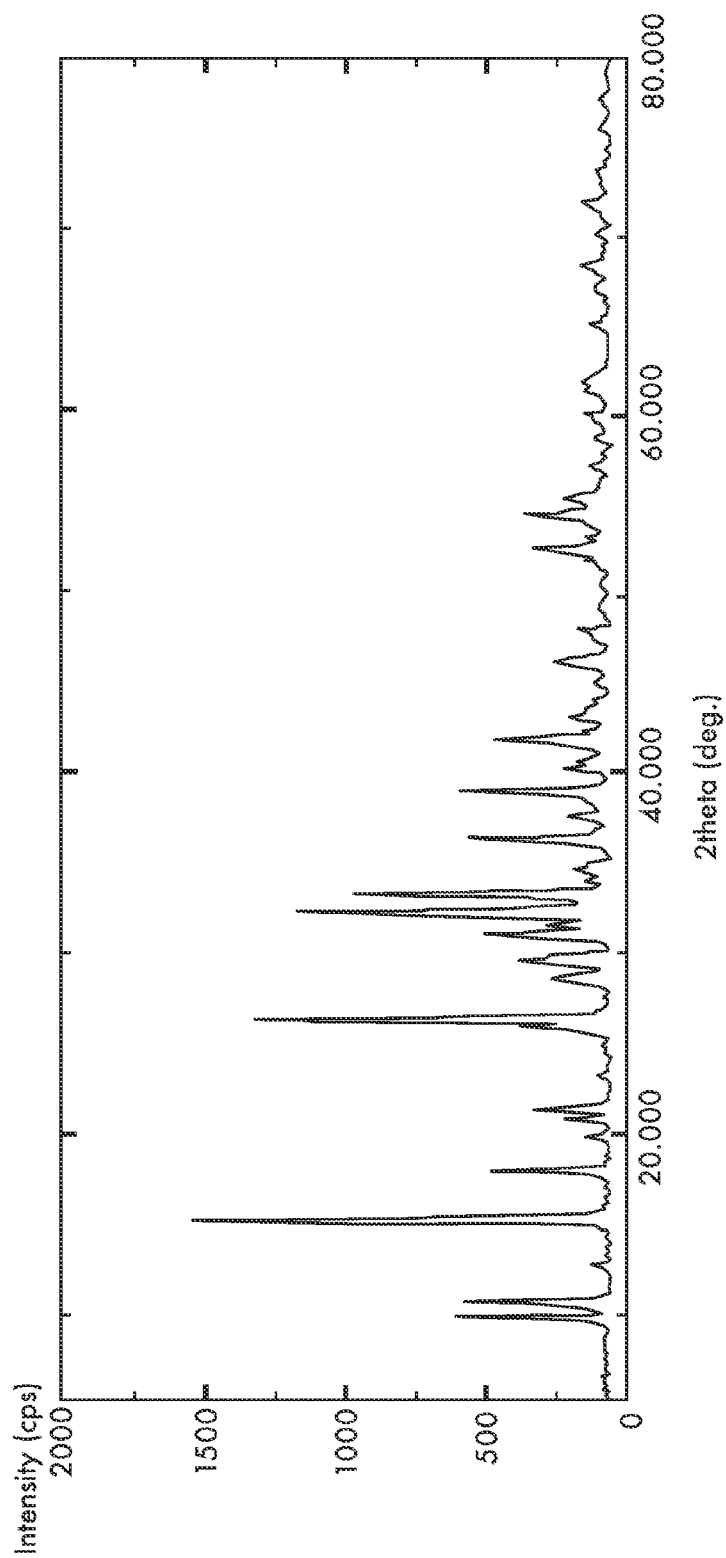

FIG. 10 shows the powder X-ray diffraction spectrum obtained corresponding to form III of the laevorotatory enantiomer and dextrorotatory enantiomer of modafinil respectively (Diffractometer: Miniflex Rigaku (Elexience).

Figure 11:
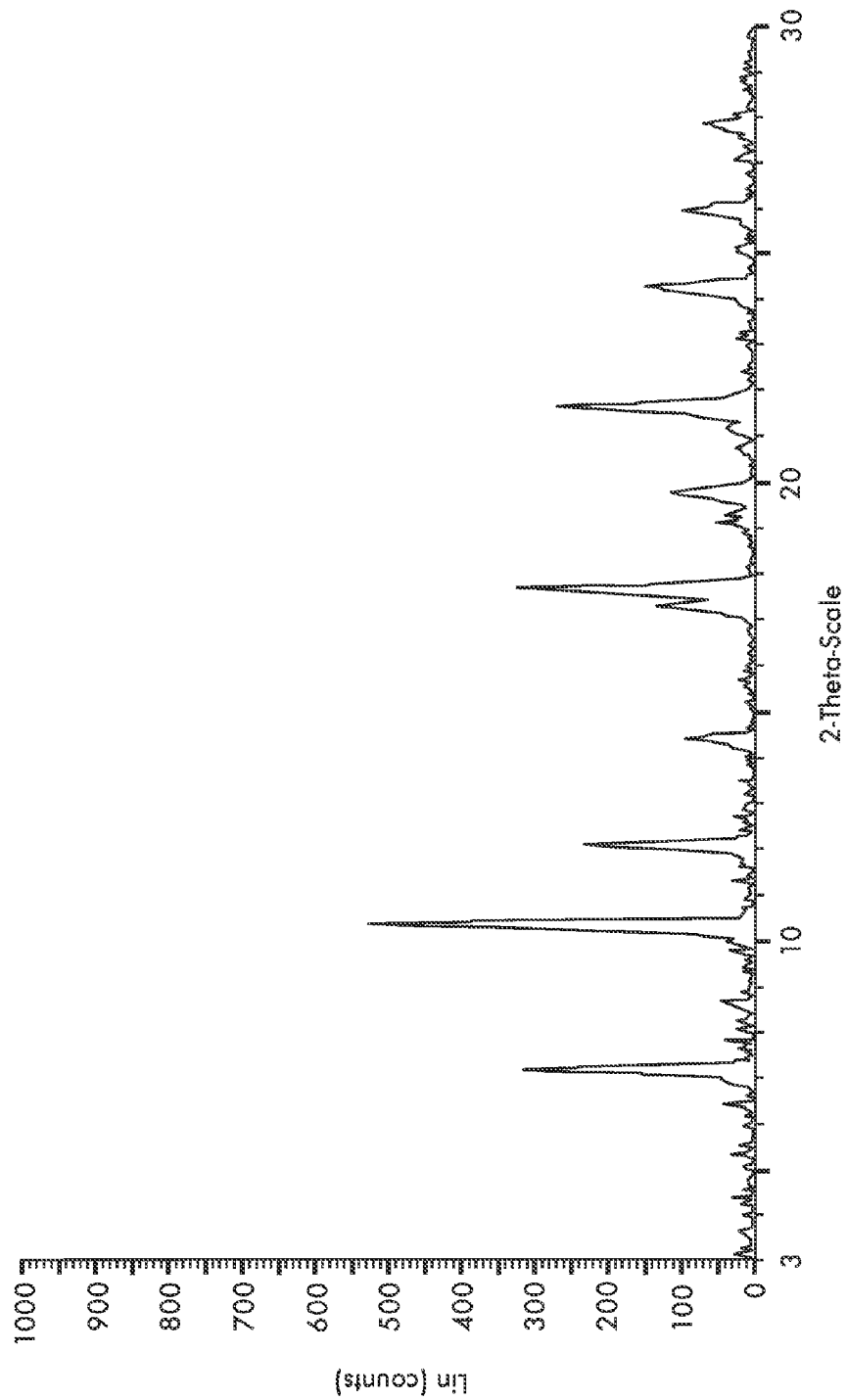

FIG. 11 shows the powder X-ray diffraction spectrum obtained corresponding to form IV of the laevorotatory enantiomer and dextrorotatory enantiomer of modafinil respectively (Diffractometer: Siemens AG).

Figure 12:
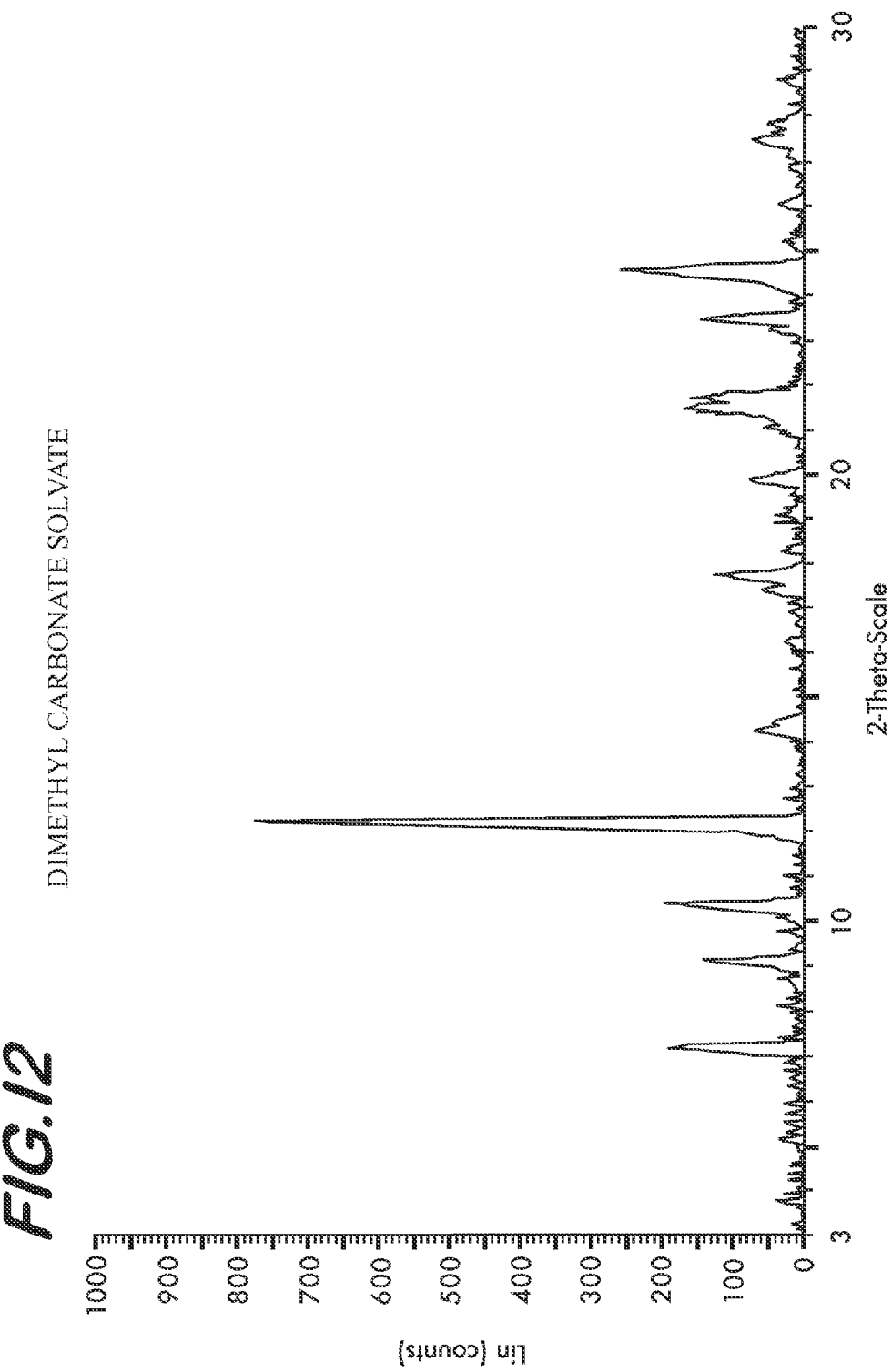

FIG. 12 shows the powder X-ray diffraction spectrum obtained corresponding to the dimethyl carbonate solvate of the laevorotatory enantiomer and the dextrorotatory enantiomer of modafinil respectively (Diffractometer: Siemens AG).

Figure 13:
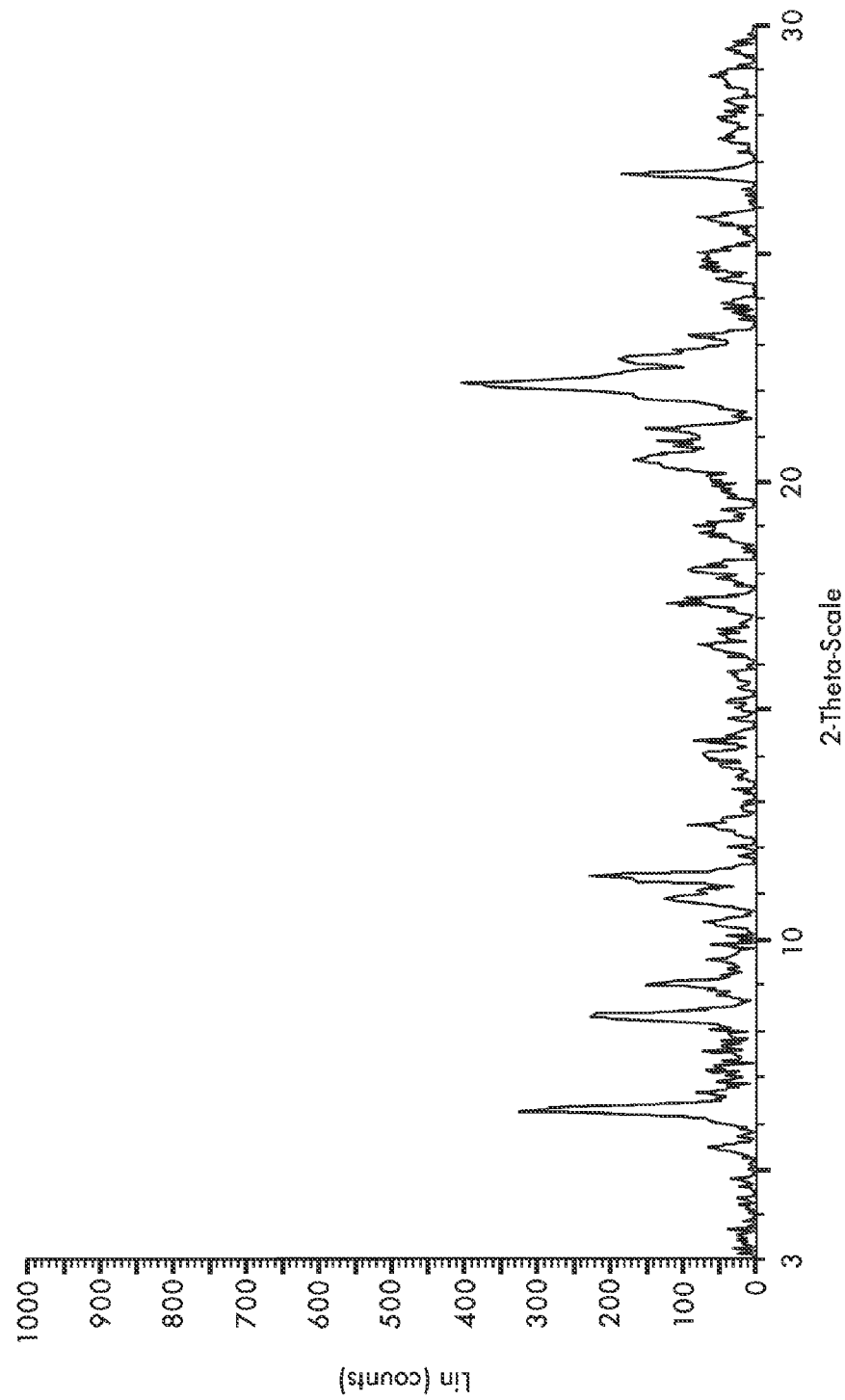

FIG. 13 shows the powder X-ray diffraction spectrum obtained corresponding to the acetonitrile solvate of the laevorotatory enantiomer and dextrorotatory enantiomer of modafinil respectively (Diffractometer: Siemens AG).

Figure 14:
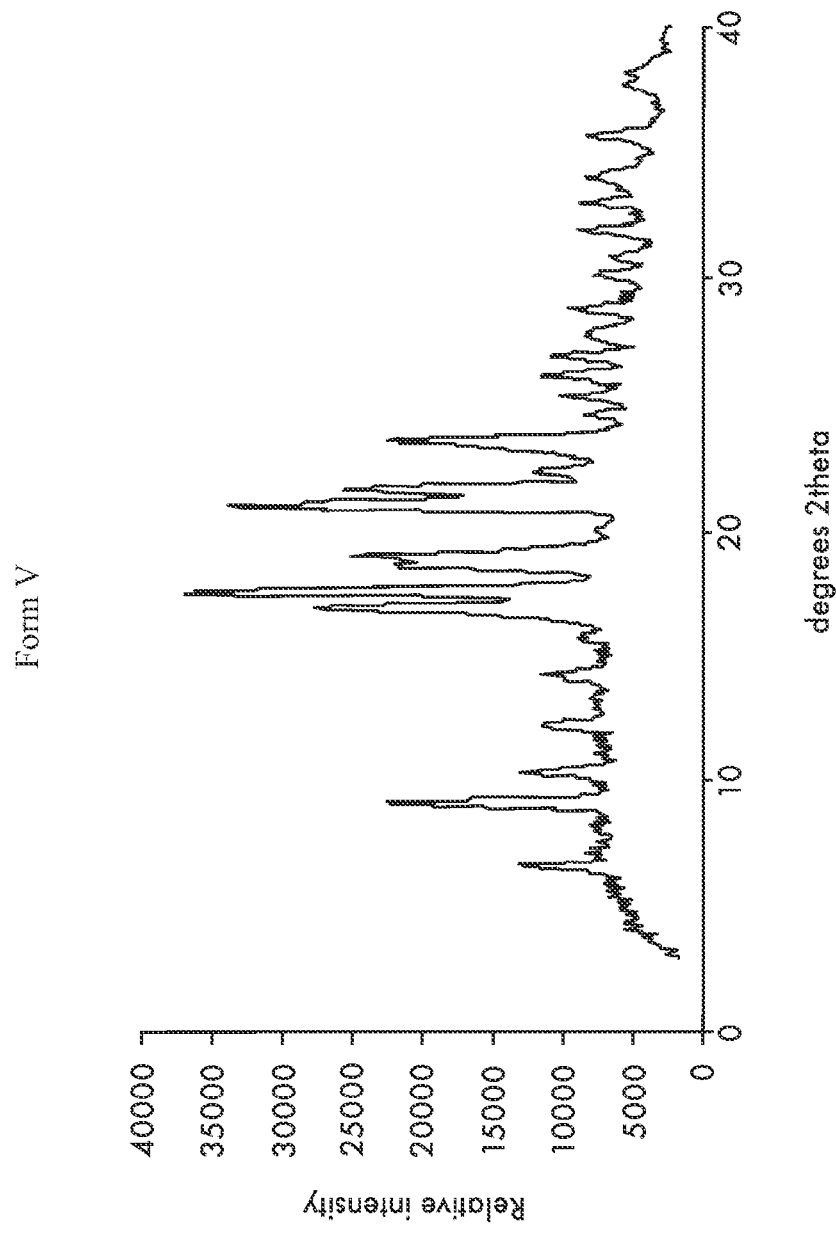

FIG. 14 shows the powder X-ray diffraction spectrum obtained corresponding to form V of the laevorotatory enantiomer of modafinil (Diffractometer: Bruker GADDS).

Figure 15:
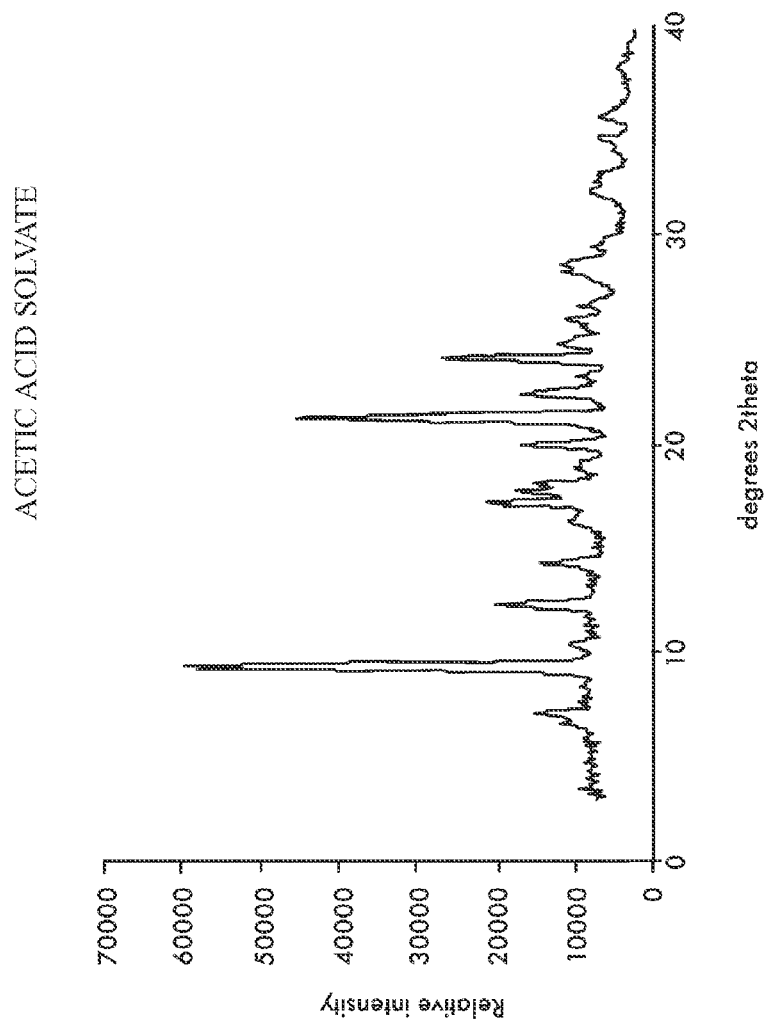

FIG. 15 shows the powder X-ray diffraction spectrum obtained corresponding to the acetic acid solvate of the laevorotatory enantiomer and the dextrorotatory enantiomer of modafinil respectively (Diffractometer: Bruker GADDS).

Figure 16:
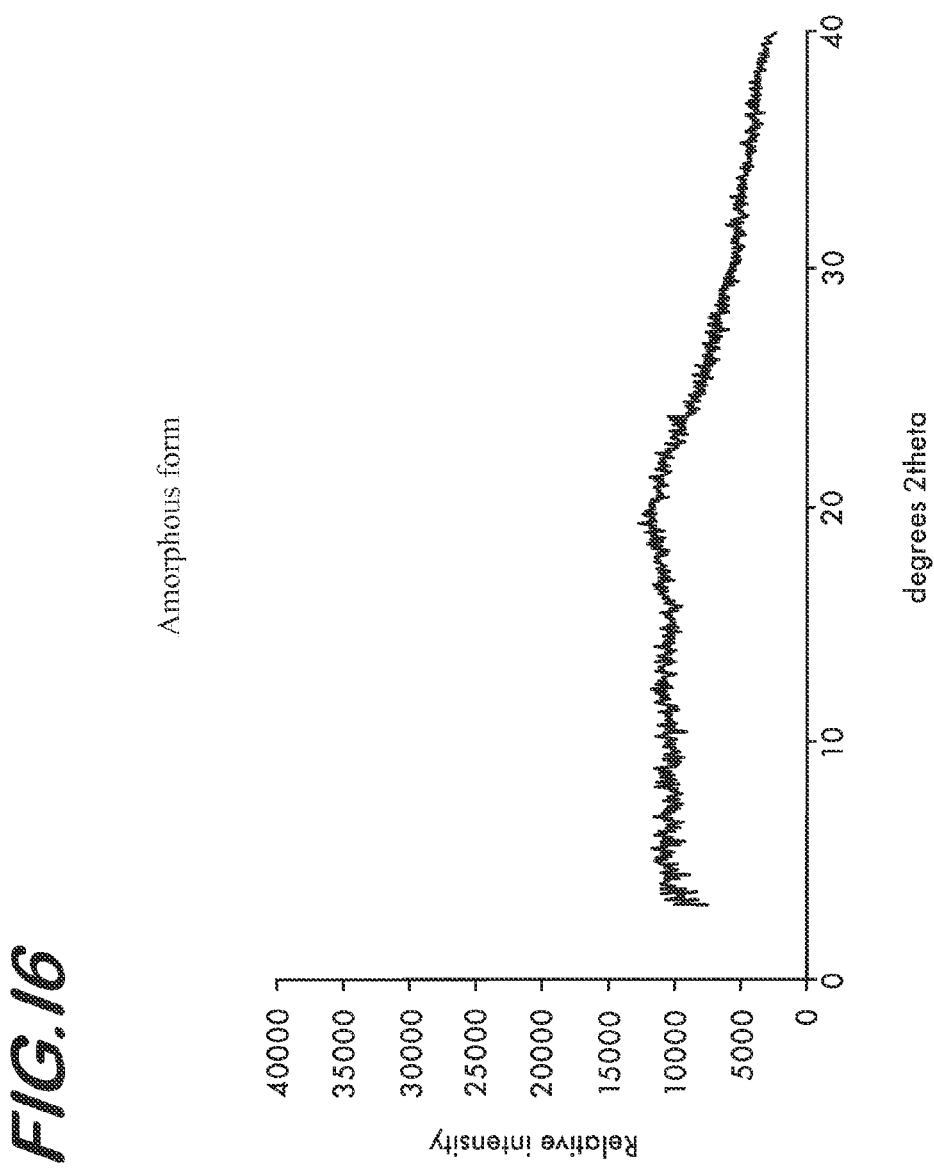

FIG. 16 shows the powder X-ray diffraction spectrum obtained corresponding to the amorphous form of the laevorotatory enantiomer and dextrorotatory enantiomer of modafinil respectively (Diffractometer: Bruker GADDS).

EXAMPLES

Preparation of Crystalline Forms of the
(−)-Modafinil Enantiomer and the (+)-Modafinil
Enantiomer Respectively General The new crystalline forms of the enantiomers of modafinil have been characterised respectively by powder X-ray diffraction spectroscopy, which provides a unique digital signature characteristic of the crystalline form investigated and can be used to distinguish it from amorphous enantiomers of modafinil and any other crystalline form of modafinil enantiomers.

The X-ray diffraction data were measured:
the D5005 system as an X-ray powder diffractometer (Siemens AG, Karlsruhe, Germany, Eva 5.0 data analysis method), with nickel-filtered copper radiation at λ=1,540 Å (with an accelerator speed of 40 KV, tube current 40 mA) and rotation of the sample during measurement (angle: 3 to 40° [2 theta] at a rate of 0.04° [2 theta]·s$^{-1}$, the step size being 0.04°, preparation of the sample with a preferential orientation).

a Miniflex Rigaku (Elexience) system as an X-ray powder diffractometer using chromium radiation, an accelerator speed of 30 KV, a tube current of 15 mA and rotation of the sample during measurement (angle: 3 to 80° [2 theta] at a rate of 0.05° [2 theta]. s$^{-1}$, the step size being 0.1°, preparation of the sample with a preferential orientation).

Using a GADDS system as a X-ray powder diffractometer (Bruker, the Netherlands), equipped with a <<Hi-Star area>> detector and equipped for the analysis of plates with 96 wells. The analyses were performed at ambient temperature using CuK$_{alpha}$ copper radiation in the region of 2 theta angles between 3 and 42°. The diffraction spectrum for each well is collected between two domains of the value for the 2 theta angle (3°≤2 Theta≤21° and 19°≤2 Theta≤42° with an exposure time of between 50 and 250 seconds.

Of course the intensity values can vary in relation to sample preparation, the assembly and the measuring instruments. The 2 theta measurement can also be affected by variations associated with the measuring instruments, so the corresponding peaks can vary from ±0.04° to ±0.2° according to the equipment. Also a person skilled in the art will appreciate having available the interplanar spacings which constitute essential data for diffraction spectra. The interplanar spacings are calculated using Bragg's relationship [(2d sin theta=nλ, in which d=the interplanar spacing (Å), λ=the wavelength of the copper radiation, theta=the angle of rotation of the crystal (in degrees)] when this relationship is satisfied.

Examples 1 to 10

Preparation of Form 10 of (−)-Modafinil and (+)-Modafinil Respectively

Example 1 a) Enantiomer I of modafinil was dissolved in polar solvents: methanol, absolute ethanol, absolute ethanol containing 3% of water, ethanol denatured with toluene (2.5%) and containing 3% of water, and water under reflux under the experimental conditions detailed in Table 1.

TABLE 1

| Solvent | Quantity of l-modafinil (g) | Volume of solvent (ml) | Yield % |
| --- | --- | --- | --- |
| Methanol | 8.37 | ≤50 | 63 |
| Absolute ethanol | 7.85 | 115 | 56 |
| Absolute ethanol + 3% of water | 5 | 70 | 54 |
| Ethanol denatured with toluene + 3% of water | 5 | 70 | 56 |
| Water | 5 | ≥400 | 88 |

After rapid cooling by quenching in a water and ice bath for 30 minutes the medium was filtered and then dried in a stove at 35° C. The crystallised product was identified by its powder X-ray diffraction spectrum as being the polymorph of form I of the l-enantiomer of modafinil.

b) Enantiomer d of modafinil (555 g), treated under the same experimental conditions as example 1a in a mixture of ethanol denatured with toluene (2 L) and water (0.1 L), crystallised in polymorphic form I as identified by its powder X-ray diffraction spectrum with a yield of 91%.

Example 2

Recrystallisation from Acetone a) 2 g of (−)-modafinil were suspended in acetone (20 ml) in a three-necked flask fitted with a condenser, a thermometer and a stirrer. The mixture was heated under reflux. The reaction mixture was stirred for 30 minutes at approximately 56° C. until the (−)-modafinil was completely dissolved. The solution was then cooled slowly at a rate of −0.5° C./min to 10° C. with stirring. The reaction mixture was filtered, and the solid obtained was dried to yield the 1 form of (−)-modafinil identified by its X-ray diffraction spectrum. Yield 62%.

b) The same experimental conditions applied to (+)-modafinil led to the acquisition of an identical X-ray diffraction spectrum.

Example 3

Recrystallisation from Methanol a) 1 g of (−)-modafinil was added to 7 ml of methanol and heated under reflux until the (−)-modafinil was completely dissolved. The reaction mixture was precipitated by adding 6 ml of water at 1° C. The suspension was stirred continuously for 1 minute and then filtered on sintered glass (No. 3). The solid isolated was dried to yield form I of (−)-modafinil identified by its X-ray diffraction spectrum. Yield 55%.

b) The same experimental conditions applied to (+)-modafinil led to the acquisition of an identical X-ray diffraction spectrum.

Example 4

Recrystallisation from Methanol (2$^{nd}$ Example)

a) 2.5 g of (−)-modafinil were added to 90 ml of methanol and heated under reflux until the (−)-modafinil was completely dissolved. The clear solution was added to 200 ml of water at 1° C. and kept stirred for 10 min. The reaction mixture was filtered and the recovered solid was dried to yield form I of (−)-modafinil identified by its X-ray diffraction spectrum. Yield 78%.

b) The same experimental conditions applied to (+)-modafinil led to the acquisition of an identical X-ray diffraction spectrum.

Example 5

Recrystallisation from 1-4 Dioxan a) 20 mL of 1-4 dioxan were placed in a 50 mL flask and placed under reflux. 2 g of (−)-modafinil were added in order to achieve saturation; stirring was provided by a magnetic bar (300 rpm). The whole was cooled after total dissolution of the (−)-modafinil using a cooling gradient of −0.5° C./min down to 20° C. The crystals obtained were filtered on sintered glass and identified as being form I by its X-ray diffraction spectrum. Yield 51%.

b) The same experimental conditions applied to (+)-modafinil led to the acquisition of an identical X-ray diffraction spectrum.

Example 6

Recrystallisation from a Mixture of Ortho, Meta and Para Xylene a) 180 mL of a mixture of ortho, meta and para xylene were placed in a 250 mL flask and placed under reflux. 0.5 g of (−)-modafinil were added to achieve saturation; stirring was provided by a magnetic bar (300 rpm). The whole was cooled after total dissolution of the (−)-modafinil using a cooling gradient of −0.5° C./min down to 15° C. The crystals obtained were filtered on sintered glass and identified as being form I by its X-ray diffraction spectrum. Yield 26%.

b) The same experimental conditions applied to (+)-modafinil led to the acquisition of an identical X-ray diffraction spectrum.

Example 7

Recrystallisation from Ethyl Acetate a) 100 mL of ethyl acetate were placed in a 250 mL flask and placed under reflux; 2 g of (−)-modafinil were added in order to achieve saturation; stirring was provided by a magnetic bar (300 rpm). The whole was cooled after total dissolution of the (−)-modafinil using a cooling gradient of −0.5° C./min down to 20° C. The crystals obtained were filtered on sintered glass and identified as being form I by its X-ray diffraction spectrum. Yield 66%.

b) (+)-modafinil (3 g) was dissolved in ethyl acetate (100 ml) under reflux. After cooling by quenching in a water and ice bath for 30 minutes, the medium was filtered and then dried in a stove at 50° C. under vacuum. The crystallised product was identified by its powder X-ray diffraction spectrum as being the polymorph of form I of (+)-modafinil.

Example 8

From Other Polymorphic Forms a) CRL 40982 form IV (0.5 g) and CRL 40982 form II (0.5 g) yielded form I by heating to 100° C.

Furthermore the pure form I of (−)-modafinil can be prepared by taking up a mixture of (−)-modafinil form I (0.5 g) and form II (0.5 g) and form III (0.5 g) in acetone (20 ml) for a sufficient time to achieve complete conversion (3 days).

In the two procedures form I was identified by its powder X-ray diffraction spectrum.

b) The use of (+)-modafinil (CRL 40983) under the same conditions yielded the same results.

Example 9

From Acetonitrile Solvate a) 1 g of acetonitrile solvate of (−)-modafinil heated to 100° C. for 8 hours converted into a white solid identified as being (−)-modafinil form I by its powder X-ray diffraction spectrum.

b) The use of (+)-modafinil (CRL 40983) under the same conditions led to the same results.

Example 10

From Monodimethyl Carbonate Solvate a) 1 g of the monodimethyl carbonate solvate of (−)-modafinil heated to 110° C. for 16 hours converted into a white solid identified as being (−)-modafinil form I by its powder X-ray diffraction spectrum.

b) The use of (+)-modafinil (CRL 40983) under the same conditions led to the same results.

Examples 11 to 12

Preparation of Form II (CRL 40982 Form II) of (−)-Modafinil and (CRL 40983 Form II) of (+)-Modafinil Respectively

Example 11

Through Rapid Cooling a) Modafinil enantiomer l was dissolved under reflux in the solvents: ethyl acetate, isopropanol, n-propanol and ethanol denatured with toluene (2.5%), according to the experimental conditions detailed in Table 2.

TABLE 2

| Solvent | Quantity of l-modafinil (g) | Volume of solvent (ml) | Yield % |
|---|---|---|---|
| Ethyl acetate | 6.33 | 385 | 53 |
| Isopropanol | 8 | 110 | 69 |
| n-propanol | 7.85 | 65 | 70 |
| Ethanol denatured with toluene (2.5%) | 5 | 80 | 54 |

After cooling by quenching in a water and ice bath for 30 minutes, the medium was filtered and then dried in a stove at 35° C. In each experimental procedure the crystallised product was identified by its powder X-ray diffraction spectrum as being the form II polymorph (CRL 40982 form II) of the 1-enantiomer of modafinil.

b) The d enantiomer of modafinil (3.02 g) was dissolved in 100 ml of isopropanol under reflux and then cooled by quenching in a water and ice bath for 30 minutes, filtered and dried under vacuum in a stove at 50° C. Under these experimental conditions (+)-modafinil crystallised into polymorphic form II (CRL 40983 form II) identified by its powder X-ray diffraction spectrum.

Example 12

By Cooling from Isopropanol a) 100 mL of isopropanol was placed in a 250 mL flask which was placed under reflux and then 3 g of (−)-modafinil were added so as to achieve saturation, the mixture was stirred using a magnetic bar (300 rpm). After total dissolution of the (−)-modafinil the solution was slowly cooled to 20° C. at a cooling gradient of −0.5° C./min. The crystals obtained were filtered on sintered glass. The crystallised product was identified by its powder X-ray diffraction spectrum as being the form II polymorph (CRL 40982 form II) of the l-enantiomer of modafinil. Yield 42%.

b) The same experimental conditions applied to (+)-modafinil led to the acquisition of an identical X-ray diffraction spectrum.

Example 13

Preparation of Form III (CRL 40982 Form III) of (−)-Modafinil and (CRL 40983 Form III) of (+)-Modafinil Respectively

Example 13

By Slow Cooling from Acetone a) The l enantiomer of modafinil (5 g) was dissolved under reflux in 90 ml of acetone. After rapid cooling by quenching in a water and ice bath for 30 minutes the medium was filtered and then dried in a stove at 35° C. The crystallised product was identified by its powder X-ray diffraction spectrum as being the form III polymorph of l-enantiomer of modafinil. Yield 61%.

b) The same experimental conditions applied to (+)-modafinil led to the acquisition of an identical X-ray diffraction spectrum.

Examples 14 to 16

Preparation of Form IV (CRL 40982 Form IV) of (−)-Modafinil and (CRL 40983 Form III) of (+)-Modafinil Respectively Example 14

Recrystallisation from Chloroform a) 20 mL of chloroform was placed in a 50 mL flask and heated under reflux. 1.5 g of (−)-modafinil were added so as to achieve saturation; stirring was provided by a magnetic bar (300 rpm). The whole was slowly cooled after total dissolution of the (−)-modafinil at a cooling gradient of −0.5° C./min down to 20° C. The crystals obtained were filtered on sintered glass and identified as being (−)-modafinil form IV by its powder X-ray diffraction spectrum.

b) The same experimental conditions applied to (+)-modafinil led to the acquisition of an identical X-ray diffraction spectrum.

Example 15

Recrystallisation from Methylethylketone a) 100 mL of methylethylketone was placed in a 250 mL flask and heated under reflux. 2 g of (−)-modafinil were added so as to achieve saturation; stirring was provided by a magnetic bar (300 Rpm). The whole was slowly cooled after total dissolution of the (−)-modafinil at a cooling gradient of −0.5° C./min down to 20° C. The crystals obtained were filtered on sintered glass and identified as being (−)-modafinil form IV by its powder X-ray diffraction spectrum.

b) The same experimental conditions applied to (+)-modafinil led to the acquisition of an identical X-ray diffraction spectrum.

Example 16

Recrystallisation from Tetrahydrofuran 20 mL of tetrahydrofuran was placed in a 50 mL flask which was heated under reflux. 1 g of (−)-modafinil was added so as to achieve saturation; stirring was provided by a magnetic bar (300 Rpm). The whole was slowly cooled after total dissolution of the (−)-modafinil with a cooling gradient of −0.5° C./min down to 10° C. The crystals obtained were filtered on sintered glass and identified as being (−)-modafinil form IV by its powder X-ray diffraction spectrum.

Examples 17 and 17B

Preparation of Form V (CRL 40982 Form V) of (+)-Modafinil and (CRL 40983 Form V) of (+)-Modafinil Respectively Operating Procedure for Examples 17 and 17 b A methanol solution of the d enantiomer of modafinil (150 mg/ml) was distributed over a 96-well plate and then the methanol was evaporated under slight vacuum before adding 25 μl of various solvents (concentration=3.75 mg/25 μL of solvent) at ambient temperature. The multi-well plates were made of stainless steel (316 L) and each sealed well contained a total volume of 50 μL. The plate was heated to an initial temperature of 60° C. with a temperature gradient of 4.8° C./min. After 30 minutes the plate was cooled slowly (−0.6° C./min) or rapidly (−300° C./min) until a final temperature of 3° C. was achieved, and it was then held at that final temperature for a minimum of 1 hour or a maximum of 48 hours. The solvent was evaporated under vacuum (nitrogen atmosphere) and the crystallised product was analysed.

Example 17

Recrystallisation from 2-propanone d-modafinil crystallised from 2-propanone in accordance with the operating conditions above by applying slow cooling (−0.6° C./min) and holding the temperature at 3° C. for 1 hour. The crystals were identified as being (+)-modafinil form V (CRL 40983 form V) by its powder X-ray diffraction spectrum.

Example 17b

Recrystallisation from Tetrahydrofuran (THF)

d-modafinil crystallised from THF in accordance with the operating conditions above by applying rapid cooling (−300° C./min) and holding the temperature at 3° C. for 1 hour. The crystals were identified as being (+)-modafinil form V (CRL 40983 form V) by its powder X-ray diffraction spectrum.

Examples 18 to 19

Preparation of (−)-Modafinil Solvates and of (+)-Modafinil

Example 18

Preparation of the Dimethyl Carbonate Solvate of (−)-Modafinil a) 20 ml of dimethyl carbonate were added to 2 g of (−)-modafinil and refluxed. The reaction mixture was stirred for 10 minutes until the (−)-modafinil completely dissolved. The solution was cooled slowly (−0.5° C./min) down to 10° C. with stirring. The reaction mixture was then filtered through sintered glass (No. 3). Analysis of the dimethyl carbonate solvate of modafinil yielded a mass of approximately 24% starting from around 50° C. down to 110° C. The stoichiometry of the dimethyl carbonate solvate is therefore 1-1. This is therefore a true solvate, identified as being the dimethyl carbonate solvate of (−)-modafinil by its powder X-ray diffraction spectrum. Yield 88%.

b) The same experimental conditions applied to (+)-modafinil led to the acquisition of an identical X-ray diffraction spectrum.

Example 19

Preparation of the Acetonitrile Solvate of (−)-Modafinil a) Crystals of polymorphic form I of (−)-modafinil were suspended in acetonitrile for 3 days at 20° C. The solid recovered was identified as an acetonitrile solvate by X-ray diffraction. The solvate corresponded to a true solvate having a stoichiometry of 1-1, identified as being the acetonitrile solvate of (−)-modafinil by its powder X-ray diffraction spectrum. Yield 92%.

b) The same experimental conditions applied to (+)-modafinil led to the acquisition of an identical X-ray diffraction spectrum.

Example 20

Preparation of the Acetic Acid Solvate a) 75 mg of d or l-modafinil were suspended in acetic acid in Minimax reactors in order to achieve a concentration of 15% (weight/volume). The crystallisation medium, which was constantly stirred, was raised to an initial temperature of 60° C. or 80° C. using a temperature gradient of 3° C./min. After 30 minutes the medium was cooled slowly (−0.6° C./min) or rapidly (−300° C./min) until a final temperature of 3° C. was obtained, and was then held at this final is temperature for a minimum of 1 hour or a maximum of 48 hours. Under these experimental conditions the acetic acid solvate was obtained and identified by its powder X-ray diffraction spectrum.

b) The same experimental conditions applied to (+)-modafinil led to the acquisition of an identical X-ray diffraction spectrum.

Example 21

Preparation of the Amorphous Form of (−) and of (+)-Modafinil

The solvate of (−) or (+)-modafinil obtained in example 20 was converted into the amorphous form by heating at 120° C. for 3 hours. The powder X-ray diffraction spectrum obtained is shown in FIG. 16.

Examples 22 to 29

Resolution of (±)-Modafinil Acid by Preferential Crystallisation

Using the AS3PC Method in Ethanol

Conditions Associated with the Equilibria
Solubility of the Racemic Mixture in Ethanol:

| Temperature (° C.) | 10.0 | 20.0 | 30.0 |
|---|---|---|---|
| Solubility by mass (%) | 3.0 | 4.1 | 5.96 |

Solubility of the pure (+)-antipode = 1.99% at 20° C.; ratio α = 2.06
Coordinates of point L = Concentration: 5.96%. temperature: 30° C.

Change in $T_{HOMO}$ with Enantiomer Excess=(Racemic Mixture/(Solvent+Racemic Mixture))=5.96%=Constant

| Enantiomer excess | 0 | 3.94 | 7.66 | 11.1 |
|---|---|---|---|---|
| $T_{HOMO}$ (° C.) | $T_L$ = 30 | 32.4 | 34.5 | 36.3 |

Conditions Associated with the Kinetics

By adjusting $T_B$ to be closer to $T_L$ approximately 40% of the final harvest in the form of fine crystals can be thus obtained at the start of the experiment, and then only 60% of the expected final mass has to be produced. This operation is easy to carry out when the Z ratio is sufficiently high (equal to or greater than 0.8 per percentage enantiomer excess).

In the case of modafinil acid, crystallisation is carried out correctly.

$$Z = \left[\frac{d(T_{HOMO})}{de \cdot e}\right]_{(\pm)constant} = Z = \left[\frac{d(T_{HOMO})}{de \cdot e}\right]_{TLconstant} = \frac{5}{9}$$

Temperature $T_{B^1}$=33.5° C. and $T_{B^2}$=31.5° C.
Temperature $T_F$=17° C.
Cooling function=T=f(t)

| Type I cooling function | | | |
|---|---|---|---|
| Temperature (° C.) | 33.5 | 17 | 17 |
| t (min) | 0 | 60 | $T_{Filtration}$ |

| Type II cooling function | | | |
|---|---|---|---|
| Temperature (° C.) | 31.5 | 17 | 17 |
| t (min) | 0 | 60 | $T_{Filtration}$ |

In the two cases in point, from TB1 or TB2 the cooling function is a linear segment:

$T_1$=33.5−0.275 t (Type I)
$T_2$=31.5−0.24167 t (Type 2)

followed by a plateau at 17° C.

Example 22

Resolution of (±)-Modafinil Acid by the AS3PC Method at the 35 cc Scale in Ethanol Initial Conditions Enantiomer excess=11%

| Mass of solvent | Mass (±) (g) | Mass (+) (g) | Cooling function |
|---|---|---|---|
| 38.38 | 2.43 | 0.3 | Type 1 |

Duration of the plateau at $T_{B1}$ or $T_{B2}$ = 30 minutes.
Stirring speed = 200 rpm Results

| No. | Mass of the pure antipode (g) | Optical purity (%) |
|---|---|---|
| 1 | 0.61 | (+) 90.7 |
| 2 | 0.65 | (−) 89.4 |
| 3 | 0.68 | (+) 90.5 |
| 4 | 0.64 | (−) 90.6 |
| 5 | 0.65 | (+) 88.8 |
| 6 | 0.72 | (−) 91.5 |
| 7 | 0.71 | (+) 92.8 |

Mean mass of the crystals of the pure antipode = 0.66 g
Average optical purity = 90.6 %

Example 23

Resolution of (±)-Modafinil Acid by the AS3PC Method on a Scale of 400 cc in Ethanol Initial Conditions
Initial enantiomer excess=11%

| Mass of solvent | Mass (±) (g) | Mass (+) (g) | Cooling function |
|---|---|---|---|
| 511 | 32.42 | 3.99 | Type I |

Stirring speed = 200 rpm

Results

| No. | Mass of the pure antipode (g) | Optical purity (%) |
|---|---|---|
| 1 | 8.41 | (+) 89.4 |
| 2 | 8.69 | (−) 90.7 |
| 3 | 8.57 | (+) 89.8 |

Mean mass of the crystals of the pure antipode = 8.55 g
Average optical purity = 89.63%

Example 24

Resolution of (±) Modafinil Acid by the AS3PC Method on a 2 Liter Scale in Ethanol Initial Conditions
Initial enantiomer excess=11.1%

| Mass of solvent | Mass (±) (g) | Mass (+) (g) | Cooling function |
|---|---|---|---|
| 1874 | 118.4 | 14.84 | Type I |

Results

| No. | Mass of the pure antipode (g) | Optical purity (%) |
|---|---|---|
| 1 | 32.1 | (+) 89.1 |
| 2 | 32.3 | (−) 90.3 |
| 3 | 32.5 | (+) 91.2 |
| 4 | 32.9 | (−) 89.7 |
| 5 | 33.1 | (+) 90.3 |
| 6 | 32.7 | (−) 90.7 |
| 7 | 32.9 | (+) 90.6 |

Mean mass of the crystals of the pure antipode = 32.6 g
Average optical purity = 90.3%

Example 25

Resolution of (±) Modafinil Acid by the AS3PC on a 10 Liter Scale in Ethanol Initial Conditions
Initial enantiomer excess=11.7%

| Mass of solvent | Mass (±) (g) | Mass (+) (g) | Cooling function |
|---|---|---|---|
| 6481 | 408 | 51.32 | Type I or II |

Stirring speed = 200 rpm throughout the procedure using an Impeller ® moving stirrer.

Results

| No. | Mass of the pure antipode (g) | Optical purity (%) | Cycle length | Cooling function |
|---|---|---|---|---|
| 1 | (+) 121.9 | 90.5 | 103 | I |
| 2 | (−) 121.1 | 92.2 | 104 | I |
| 3 | (+) 137.6 | 91.3 | 83 | II |
| 4 | (−) 134.7 | 90.8 | 84 | II |
| 5 | (+) 135.1 | 90.6 | 83 | II |
| 6 | (−) 134.5 | 91.2 | 82 | II |

Mean mass of the crystals of the pure antipode = 130.8 g
Average optical purity = 89.9%

Using the AS3PC Method in 2-methoxyethanol

Conditions Associated with the Equilibria
Solubility of the Racemic Mixture in 2-Methoxyethanol:

| Temperature (° C.) | 10.0 | 20.0 | 30.0 | 40.0 |
|---|---|---|---|---|
| Solubility by mass (%) | 7.4 | 8 | 13.5 | 16 |

Solubility of the pure (+) antipode = 4% at 20° C. ratio α = 2.53
Coordinates of point L = Concentration: 16%. temperature: 39.4° C.

Change in $T_{HOMO}$ with Enantiomer Excess=(Racemic Mixture/(Solvent+Racemic Mixture))=16%=Constant

| Enantiomer excess | 0 | 4% | 6% | 8% |
|---|---|---|---|---|
| $T_{HOMO}$ (° C.) | $T_L$ = 39 | 44 | 46 | 48 |

Example 26

Resolution of (±)-Modafinil Acid in 2-methoxyethanol by the AS3PC Method on a 10 Liter Scale Initial Conditions
Enantiomer excess=10%
Initial temperature $T_B$: 41° C.
Filtration temperature $T_F$: 30° C.
Linear temperature gradient from 41° C. to 30° C. in 1 hour

| Mass of solvent | Mass (±) (g) | Mass (+) (g) |
|---|---|---|
| 8000 g | 1523 | 132 |

Stirring speed = 200 rpm

Results

| No. | Mass of the pure antipode (g) | Optical purity (%) |
|---|---|---|
| 1 | 269.86 | (+) 100 |
| 2 | 300 | (−) 97 |
| 3 | 348.68 | (+) 100 |
| 4 | 369.2 | (−) 99.97 |
| 5 | 413.97 | (+) 100 |
| 6 | 453.2 | (−) 95.5 |
| 7 | 423.8 | (+) 98 |
| 8 | 456 | (−) 99.7 |
| 9 | 494.6 | (+) 99.3 |
| 10 | 485.4 | (−) 100 |
| 11 | 517 | (+) 92 |
| 12 | 487.97 | (−) 95.9 |
| 13 | 471.24 | (+) 99.5 |

Mean mass of the crystals of the pure antipode = 422.4 g
Average optical purity = 98.2%

Using the AS3PC Method in Methanol

Conditions Associated with the Equilibria
Solubility of the Racemic Mixture in Methanol:

| Temperature (° C.) | 10.0 | 20.0 | 30.0 | 40.0 |
|---|---|---|---|---|
| Solubility by mass (%) | 7.4 | 9.7 | 13.9 | 25.7 |

Solubility of the pure (+) antipode = 4.9% at 20° C. ratio α = 2.53
Coordinates of point L = Concentration: 25.6%. temperature: 46.5° C.

Change in $T_{HOMO}$ with Enantiomer Excess=(Racemic Mixture/(Solvent+Racemic Mixture))=25.7%=Constant

| Enantiomer excess | 0 | 4% | 6% | 8% | 10% |
|---|---|---|---|---|---|
| $T_{HOMO}$ (° C.) | $T_L$ = 45 | 50 | 52 | 53 | 54 |

Example 27

Resolution of (±)-Modafinil Acid by the AS3PC Method on a 1 Liter Scale in Methanol
Experimental Conditions
Enantiomer excess=10%
Initial temperature $T_B$: 46.5° C.
Filtration temperature $T_F$: 30° C.
Temperature gradient: linear from 39.4° C. to 18° C. for 1 hour

| Mass of solvent | Mass (±) (g) | Mass (+) (g) |
|---|---|---|
| 1450 g | 501.5 | 55.7 |

Stirring speed = 230 rpm

Results

| No. | Mass of the pure antipode (g) | Optical purity (%) |
|---|---|---|
| 1 | 107.1 | (+) 99.7 |
| 2 | 90.9 | (−) 78.2 |
| 3 | 137.1 | (+) 72.7 |
| 4 | 125.5 | (−) 84.1 |
| 5 | 95.9 | (+) 94.0 |
| 6 | 91.6 | (−) 88.6 |
| 7 | 87.0 | (+) 85.7 |
| 8 | 92.2 | (−) 88.1 |
| 9 | 107.0 | (+) 104.2 |
| 10 | 130.6 | (−) 120.7 |
| 11 | 159.9 | (+) 111.0 |
| 12 | 123.3 | (−) 113.8 |
| 13 | 133.0 | (+) 130.3 |
| 14 | 143.0 | (−) 134.7 |
| 15 | 139.2 | (+) 128.5 |
| 16 | 159.4 | (−) 127.5 |
| 17 | 114.0 | (+) 111.5 |
| 18 | 123.4 | (−) 120.9 |
| 19 | 180.6 | (+) 99.3 |
| 20 | 114.2 | (−) 110.9 |
| 21 | 123.1 | (+) 120.6 |
| 22 | 118.4 | (−) 115.0 |
| 23 | 140.1 | (+) 135.9 |
| 24 | 186.2 | (−) 118.6 |
| 25 | 157.1 | (+) 106.8 |
| 26 | 121.2 | (−) 102.2 |
| 27 | 126.5 | (+) 122.5 |
| 28 | 106.6 | (−) 99.0 |

Mean mass of the crystals of the pure antipode = 108 g
Average optical purity = 87.5%

Using the SIPC Method in Ethanol
Conditions Associated with the Equilibria (See AS3PC Method)

Example 28

Resolution of (±) Modafinil Acid by the SIPC Method on a 2 Liter Scale with Seeding at the End of Cooling in Ethanol Initial Conditions
Initial enantiomer excess=11.8%
Temperature at which the starting mixture is a homogeneous solution
$T_D$=40° C.

| Mass of solvent | Mass (±) (g) | Mass (+) (g) | Cooling function |
|---|---|---|---|
| 1874 | 118.4 | 14.84 | 20 min from 40° C. to 17° C. = seeding temperature |

Time (plateau) at $T_F$ before adding the seeds = 0 minutes
Mass of seeds = 1%
Crystallisation time = fastest possible cooling by quenching
Stirring speed = 200 rpm throughout the procedure using an Impeller ® mobile stirrer.

Results

| No. | Mass of the pure antipode (g) | Optical purity (%) |
|---|---|---|
| 1 | 30.9 | (+) 90.4 |
| 2 | 31.5 | (−) 90.7 |
| 3 | 31.3 | (+) 91.4 |
| 4 | 31.2 | (−) 90.9 |
| 5 | 31.6 | (+) 91.5 |

Mean mass of the crystals of the pure antipode = 31.28 g
Averageoptical purity = 91%

Example 29

Resolution of (±)-Modafinil Acid by the S3PC Method on a 2 Liter Scale with Seeding During Cooling in Ethanol Initial enantiomer excess: 11.14%

| Mass of solvent | Mass (±) (g) | Mass (+) (g) | Cooling function |
|---|---|---|---|
| 1874 | 118.4 | 14.84 | 20 min from 40° C. to 17° C. |

Seeding temperature = 29° C.
Seed mass = 1%
Crystallisation time = the fastest possible cooling by quenching
Stirring speed = 200 rpm throughout the procedure using an Impeller ® mobile stirrer.

Results

| No. | Mass | Optical purity (%) before purification |
|---|---|---|
| 1 | 25.2 | (+) 84.5 |
| 2 | 24.9 | (−) 85.6 |
| 3 | 25.6 | (+) 84.6 |
| 4 | 25.2 | (−) 85.3 |
| 5 | 24.9 | (+) 85.8 |

Mean mass of the crystals of the pure antipode = 25.2 g
Average optical purity = 85.2%

Examples 30 to 32

Conversion of the Optical Enantiomers of Modafinil Acid to Alkyl Ester

This stage is illustrated through the use of (−)modafinil acid.

Examples 30 to 31

Esterification of (−)-Modafinil Acid

Example 30

In the Presence of Dimethylsulphate 3.3 liters of acetone, 0.6 liters of water, 349 g of $Na_2CO_3$ (3.29 moles), 451 g of (−)-modafinil acid (1.64 moles) were placed in a 10 liter flask and heated to achieve reflux. Then 330 ml of dimethyl sulphate (3.29 moles) were run in over half an hour. Reflux was continued for one hour and then it was allowed to cool to ambient temperature in 20 hours.

The medium was then poured on to 6.6 kg of ice. Crystallisation was immediate and after 3 hours additional stirring filtration yielded a white precipitate which was washed in 6 liters of water.

This product was taken up again in 6 liters of water and again filtered. The precipitate was dried under vacuum at 35° C. and in this way 436.3 g of methyl ester were obtained (Yield=92.3%).

Example 31

In the Presence of Methyl Chloroformate 100 g of (−)-modafinil acid (0.36 mole) and 21.6 ml of triethylamine (0.36 mole) were added to 450 ml of methanol. 30 ml of methyl chloroformate 0.36 mole) were progressively poured onto the solution obtained after dissolution of the salt.

Pouring was carried out over 15 minutes increasing from 28° C. to 35° C. (release of $CO_2$). This was stirred for 2 hours and poured onto piled ice+water (500 g/500 ml).

The ester crystallised out; after filtering and drying 94.5 g of ester was obtained.
(Yield=90.1%).

Example 32

Ammonolysis of the Alkyl Ester of Optically Active Modafinil Acid 1.63 liters of methanol denatured with toluene, 0.1 liters of water and 425.1 g of methyl ester (1.474 moles) were placed in a 4 liter double jacket reactor.

The temperature was raised to 30° C. and bubbling of ammonia was begun is maintaining this temperature. The operation lasted 1 hour and 45 minutes and the mass of ammonia introduced was 200 g. Stirring was maintained for 21 hours 30 minutes, and then it was cooled with the temperature being set to 0° C.

The medium was then filtered on No. 3 sintered glass and 57.2 g was obtained straight away, together with a filtrate which was evaporated to dryness. The residue was taken up in 1.2 liters of ethanol denatured with toluene and after filtration a second amount of 308.6 g was obtained.

First Crystallisation:

The two amounts were pooled and recrystallised in 1.83 liters of ethanol denatured with toluene. Hot filtration yielded a filtrate which when cooled yielded a product which was filtered and dried under vacuum at 30° C. 162.2 g of a white product was obtained.

Second Crystallisation:

These 162.2 g were mixed with 810 ml of ethanol denatured with toluene and heated under reflux to achieve complete dissolution. This was then allowed to crystallise by cooling with ice and then filtered through No. 4 sintered glass and dried under vacuum at 30° C. 147.3 g (−)-modafinil (CRL 40982) was obtained.

Yield=36.6%.

Characteristics:

Rotation power=−18.6 (4.9% solution in methanol)

Melting point=163° C.

Examples 33 to 34

Crystalline Structures

Example 33

Structure of Modafinil Acid

Modafinil crystals were obtained from acetone. This phase has the following characteristics:

Hexagonal $P3_1$ or $P3_2$ depending upon the enantiomer, the modafilil is therefore a conglomerate, a=9.55, b=9.55, c=13.14 Å

$\alpha$=90,000, $\beta$=90,000, $\gamma$=120,000°

The diffraction intensities were measured using an automatic SMART APEX (Brucker) diffractometer at 20° C.

The structure was resolved using the set of Saintplus, Sadabs, Shelxs software packages.

The unusual nature of this spatial group in the case of chiral organic molecules must be emphasised.

The pattern repeats three times in the crystal lattice, so again Z=1. The molecules are linked together by hydrogen bonds via the acid and sulphoxide groups. It may be commented that the strongest interactions (the hydrogen bonds) wrap around the ternary helical axis along the crystallographic direction z.

Example 34

Structure of (−) and (+)-Modafinil Form I

The crystalline structure of (+)-modafinil form I, identified as being identical to that of (−)-modafinil form I, was determined. It has the following properties:

Crystalline system=monoclinic,

Spatial group=$P2_1$ a=5.6938, b=26.5024, c=9.3346 Å

$\beta$=105.970°

The diffraction intensities were measured using an automatic SMART APEX (Brucker) diffractometer at 20° C.

The invention claimed is:

1. A dextrorotatory enantiomer of modafinil in a polymorphic form that produces a powder X-ray diffraction spectrum comprising intensity peaks corresponding to interplanar spacings at about 5.23, 5.03, 4.22, and 4.10 (Å).

2. The dextrorotatory enantiomer of modafinil according to claim 1, wherein the powder X-ray diffraction spectrum further comprises intensity peaks corresponding to interplanar spacings at about 9.63, 4.74, 4.66 and 3.77 (Å).

3. A polymorphic form of the dextrorotatory enantiomer of modafinil that produces a powder X-ray diffraction spectrum comprising reflections at about 16.95, 17.64, 21.06 and 21.67 degrees 2θ.

4. The polymorphic form according to claim 3, wherein the powder X-ray diffraction spectrum further comprises reflections at about 9.17, 18.69, 19.03 and 23.61 degrees 2θ.

5. A composition consisting essentially of a polymorphic form of the dextrorotatory enantiomer of modafinil that produces a powder X-ray diffraction spectrum comprising intensity peaks corresponding to interplanar spacings of about 5.23, 5.03, 4.22 and 4.10 (Å).

6. The composition according to claim 5, wherein the powder X-ray diffraction spectrum further comprises intensity peaks corresponding to interplanar spacings of about 9.63, 4.74, 4.66 and 3.77 (Å).

7. A composition consisting essentially of a polymorphic form of the dextrorotatory enantiomer of modafinil that produces a powder X-ray diffraction spectrum comprising reflections at about 16.95, 17.64, 21.06 and 21.67 degrees 2θ.

8. The composition according to claim 7, wherein the powder X-ray diffraction spectrum further comprises reflections at about 9.17, 18.69, 19.03 and 23.61 degrees 2θ.

9. A Form V polymorph of the dextrorotatory enantiomer of modafinil.

10. A composition comprising the Form V polymorph of claim 9.

11. A composition comprising the Form V polymorph of claim 9, wherein said composition is substantially free of other polymorphic forms of the dextrorotatory enantiomer of modafinil.

12. A composition consisting essentially of the Form V polymorph of claim 9.

13. A pharmaceutical composition comprising one or more pharmaceutically acceptable excipients and the Form V polymorph of claim 9.

14. A pharmaceutical composition comprising one or more pharmaceutically acceptable excipients and an active ingredient consisting essentially of the Form V polymorph of claim 9.

15. A process for preparing the Form V polymorph of claim 9, comprising the steps of: (a) providing a solution of the dextrorotatory enantiomer of modafinil dissolved in a hot solvent; (b) cooling the solution from step (a) to produce crystals; (c) isolate the crystals of said Form V polymorph that are formed in step (b); wherein the solvent of step (a) is selected from 2-pentanone and tetrahydrofuran.

* * * * *